United States Patent
Irie et al.

(10) Patent No.: US 6,509,003 B2
(45) Date of Patent: *Jan. 21, 2003

(54) REAGENTS FOR THE DETERMINATION OF CEREBRAL REGIONAL ACETYLCHOLINESTERASE ACTIVITY

(75) Inventors: Toshiaki Irie, Yotsukaido (JP); Kiyoshi Fukushi, Funabashi (JP); Hiroki Namba, Chiba (JP); Masaomi Iyo, Hamamatsu (JP); Nobuo Ikota, Tokyo (JP); Shinichiro Nagatsuka, Ibaraki (JP); Takao Ueda, Ibaraki (JP); Masaru Nishiura, Chiba (JP); Keizo Takatoku, Chiba (JP); Isamu Yomoda, Chiba (JP)

(73) Assignees: Daiichi Pure Chemicals Co., Ltd., Tokyo (JP); Daiichi Radioisotope Laboratories, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/764,263

(22) Filed: Jan. 19, 2001

(65) Prior Publication Data

US 2002/0127180 A1 Sep. 12, 2002

Related U.S. Application Data

(62) Division of application No. 09/424,868, filed as application No. PCT/JP98/02538 on Jun. 9, 1998, now Pat. No. 6,306,882.

(30) Foreign Application Priority Data

Jun. 11, 1997 (JP) .............................. 9-153452

(51) Int. Cl.⁷ .................... A61K 51/04; A61K 31/445; A61K 49/10; C07D 211/40
(52) U.S. Cl. .................... 424/1.85; 514/327; 546/242; 546/221; 546/222; 424/9.44
(58) Field of Search .................... 514/327; 546/242; 546/221, 222; 424/1.85, 9.44

(56) References Cited

FOREIGN PATENT DOCUMENTS

JP 63-39860 * 2/1988

OTHER PUBLICATIONS

Toshiaki IRIE, et al., J. Nucl. Med., vol. 37, No. 4, pp. 649–655, "Brain Acetylcholinesterase Activity: Validation of a Pet Tracer in a Rat Model of Alzheimer's Disease", Apr. 1996.

Journal of Medicinal Chemistry, vol. 16(2), 156–159(1973).

* cited by examiner

Primary Examiner—Evelyn Mei Huang
(74) Attorney, Agent, or Firm—Oblon, Spivak, McClelland, Maier & Neustadt, P.C.

(57) ABSTRACT

The present invention relates to N-alkylpiperidine derivatives represented by general formula (1) or (2);

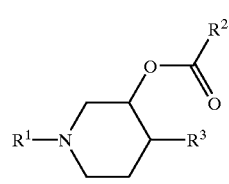

(1)

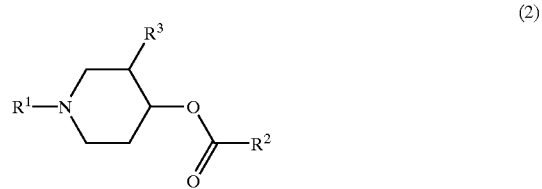

(2)

wherein $R^1$ represents optionally fluorinated lower alkyl; $R^2$ represents lower alkyl; and $R^3$ represents alkenyl substituted at the 1-position with hydroxy, lower alkoxy, lower alkoxyalkyloxy, lower alkoxyalkyloxyalkyloxy, or lower alkanoyloxy and substituted at the end with radioactive iodine, or alkenyloxymethyl substituted at the end with a radioactive iodine reagent containing the same for assaying central local AchE activity; a method for assaying the central local AchE activity; and labeled precursors of the above compounds. After easily passing through the blood-brain barrier, these compounds are hydrolyzed specifically by AchE in the brain into alcohols, which are then captured by the brain. In contrast, alcohols formed outside the brain do not migrate into the brain. The compounds of the invention emit γ-rays at an appropriate energy level. These characteristics make the compounds highly useful as tracers for SPECT in assaying the central AchE activity.

19 Claims, 4 Drawing Sheets

5 MINUTES AFTER ADMINISTRATION OF COMPOUND (46)

5 MINUTES AFTER ADMINISTRATION OF COMPOUND (47)

30 MINUTES AFTER ADMINISTRATION OF COMPOUND (47)

REAGENTS FOR THE DETERMINATION OF CEREBRAL REGIONAL ACETYLCHOLINESTERASE ACTIVITY

CROSS-REFERENCE TO RELATED APPLICATIONS

The present application is a Divisional Application of U.S. Ser. No. 09/424,868, filed Dec. 8, 1999, now U.S. Pat. No. 6,306,882, which in turn is a 371 of PCT/JP98/02538 filed Jun. 9, 1998.

TECHNICAL FIELD

The present invention relates to N-alkylpiperidine derivatives and reagents including the derivatives used for the determination of cerebral regional acetylcholinesterase (AchE) activity.

BACKGROUND ART

Cerebral cholinergic nerve system plays an important role in memory function. Degeneration of this nerve system is thought to be implicated in memory impairment seen in dementing disorders such as Alzheimeer's disease. The AchE activity has been found to be reduced in accordance with the decreased cholinergic function in the brain. The determination of cerebral regional AchE activity may, therefore, contribute greatly to clinical diagnosis, therapeutic evaluation and pathological elucidation of dementing and/or age-related neurological disorders.

Conventionally, AchE activity in the brain has been determined enzymatically or histochemically using homogenate or sections of postmortem brain tissue. Lipophilic acetylcholine analogs labeled with radionuclide have also been used to determine AchE activity in the brain by using autoradiagraphy or emission tomography (Japanese Patent Application laid-open No. 327497/1994). The emission tomographic method allows non-invasive determination of AchE activity in the living brain in both human and animal subjects. This method has been found to be of merit for clinical diagnosis or development of therapeutic drugs for degenerative disorders of cholinergic nerve system including Alzheimer's disease (Namba et. el., Brain Res., 667:278–282, 1994, Irie et. al., J. Nucl. Med., 37:649–655, 1996).

The radiolabeled compounds used in the method described in above publications must have following characteristics:

(1) Highly lipophilic to pass through the blood-brain barrier easily;
(2) Being specifically hydrolyzed by AchE in the brain;
(3) Being hydrolyzed to less lipophilic alcohol that is trapped in the brain; and
(4) Negligible cerebral incorporation of the hydrolyzed alcohol formed outside the brain.

The above application have shown the following radiolabeled compounds satisfying the above requirements; N-methylpiperidinyl-3-acetate, N-methylpiperidinyl-3-propionate, N-methylpiperidinyl-4-acetate and N-methylpiperidinyl-4-propionate, each of which has N-methyl group labeled with $^{14}C$. By using these compounds, autoradiographic determination of cerebral AchE activity ahs been achieved in rats. Furthermore, positron emission tomography (PET) using the $^{11}C$ labeled compound has been done for non-invasive determination of cerebral AchE activity in living subjects (Iyo el. Al., Lancet, 349:1805–1809, 1997)

The conventional lipophilic acetylcholine analogs including the compounds described above, however, allow only $^{11}C$-labeling to give practically available radiolabeled compounds used for non-invasive determination of cerebral AchE activity. Therefore, PET using positron camera is the only selection allowed to be used for clinical application to human subjects. Because of the short half-life of $^{11}C$ (about 20 min), PET scanning is restricted to performing in a facility with a cyclotron for radioisotope production. Meanwhile, single photon emission computed tomography (SPECT) using gamma camera is widely used for clinical practice, so the development of a radiolabeled compound applicable to SPECT has been demanded.

DISCLOSURE OF THE INVENTION

The present inventors have performed earnest studies on compounds labeled with an appropriate gamma-ray emitting radionuclide with a view to developing an AchE activity imaging SPECT agent fulfilling the required characteristics, and have found novel N-alkylpiperidine derivatives labeled with radioactive iodine.

The present invention provides N-alkylpiperidine derivatives and their salts represented by the following general formula (1) or (2);

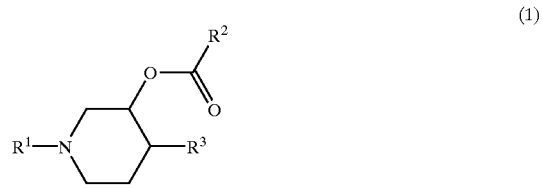

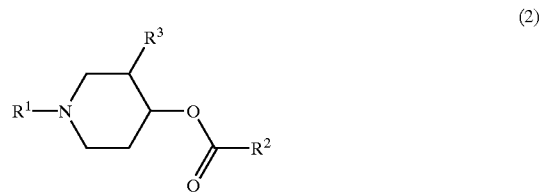

wherein $R^1$ represents a lower alkyl group which may be substituted by a fluorine atom; $R^2$ represents a lower alkyl group; and $R^3$ represents an alkenyl group which is substituted at its 1-position by a hydroxy group, a lower alkoxy group, a lower alkoxyalkyloxy group, a lower alkoxyalkyloxyalkyloxy group, or a lower alkanoyloxy group and is substituted at the end by radioactive iodine, or an alkenyloxymethyl group which is substituted at an the end by radioactive iodine.

The present invention also provides a reagent for the determination of AchE activity including the N-alkylpiperidine derivatives and their salts.

The present invention also provides the method for the determination of cerebral regional AchE activity using the N-alkylpiperidine derivatives and their salts.

The present invention also provides precursors of the radioactive N-alkylpiperidine derivatives and their salts, represented by the following general formula (1P) or (2P);

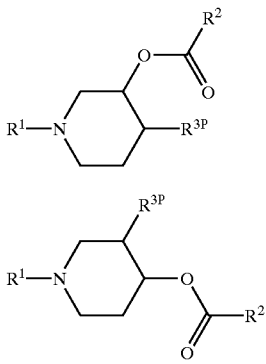

(1P)

(2P)

wherein R¹ represents an lower alkyl group which may be substituted by a fluorine atom; R² represents a lower alkyl group; and $R^{3P}$ represents an alkenyl group which is substituted at its 1-position by a hydroxy group, a lower alkoxy group, a lower alkoxyalkyloxy group, a lower alkoxyalkyloxyalkyloxy group, or a lower alkanoyloxy group and is substituted at the end by a non-radioactive halogen atom, a trialkyltin group, or a trialkylsilyl group, or an alkenyloxymethyl group which is substituted at the end by non-radioactive halogen atom, a trialkyltin group, or a trialkylsilyl group.

BRIED DESCRIPTION OF THE DRAWINGS

BEST MODES FOR CARRYING OUT THE INVENTION

Figure 1:
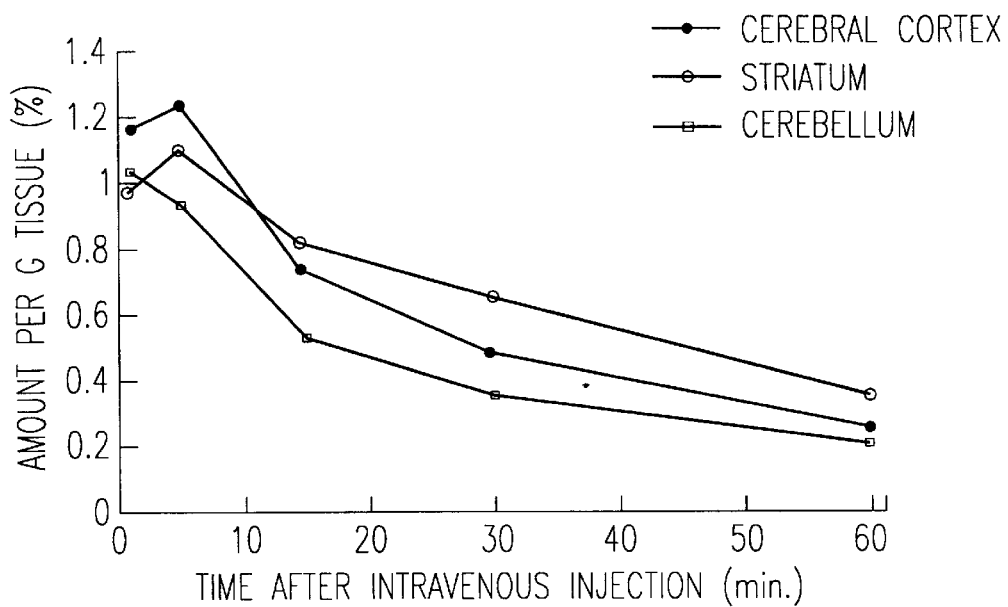
FIG. 1 shows the cerebral distribution of radioactivity in rats determined by using dissected brain tissue after the administration of one of the compounds produced by the present invention.

In the above-described formulas (1), (2), (1P), and (2P), examples of the lower alkyl groups which are represented by R¹ and which may be substituted by a fluorine atom include C1–C5 alkyl groups which may be substituted by a fluorine atom, and of these, methyl, ethyl, and fluoroethyl groups are preferred.

Examples of the lower alkyl groups represented by R² include C1–C5 alkyl groups, and of these, methyl, ethyl, propyl and isopropyl groups are preferred.

Examples of the lower alkoxy groups at the 1-position of R³ and $R^{3P}$ include C1–C5 alkoxy groups, and of these, a methoxy group is preferred. Examples of the lower alkoxyalkyloxy groups at the 1-position of R³ and $R^{3P}$ include $C_{1-5}$ alkoxy-$C_{1-5}$ alkyloxy groups, and of these, methoxymethyloxy, ethoxymethyloxy, and ethoxyethyloxy groups are preferred. Examples of the lower alkoxyalkyloxyalkyloxy groups at the 1-position of R³ and $R^{3P}$ include $C_{1-5}$ alkoxy-$C_{1-5}$ alkyloxy-$C_{1-5}$ alkyloxy groups, and of these, methoxyethyloxymethyloxy and ethoxyethyloxymethyloxy groups are preferred. Examples of the lower alkanoyloxy groups at the 1-position of R³ and $R^{3P}$ include C2–C6 alkanoyloxy groups, and of these, acetoxy and propionyloxy groups are preferred.

Examples of radioactive iodine atoms substituted at the end of R³ include $^{123}I$ and $^{131}I$, and of these, $^{123}I$ is preferred. Preferred examples of non-radioactive halogen atoms substituted at the end of $R^{3P}$ include bromine and iodine atoms. Examples of alkenyl groups in R³ and $R^{3P}$ include C2–C8 alkenyl groups, and of these, propenyl, butenyl, and pentenyl groups are preferred. Examples of alkenyloxymethyl groups in R³ and $R^{3P}$ include C3-C9 alkenyloxymethyl groups, and of these, propenyloxymethyl and butenyloxymethyl groups are preferred, and each of these compounds preferably has a double bond at the end. In addition, an alkyl group in a trialkyltin or trialkylsilyl group is preferably a C1–C5 alkyl group.

$R^{3P}$ is preferably a C2–C8 alkenyl group which is substituted at the 1-position by a hydroxy group, a lower alkoxyalkyloxy group, a lower alkoxyalkyloxyalkyloxy group, or a lower alkanoyloxy group, and is substituted by a non-radioactive halogen atom, a trialkyltin group, or a trialkylsilyl group at the end. R³ is preferably a C2–C8 alkenyl group which is substituted at the 1-position by a hydroxy group, a lower alkoxyalkyloxy group, a lower alkoxyalkyloxyalkyloxy group, or a lower alkanoyloxy group, and is substituted by a radioactive iodine atom at the end.

Particularly preferred examples of the compound (1) of the present invention include N-methyl-3-acetoxy-4-(1-hydroxy-3-$^{123}$I-2-propenyl)piperidine, N-methyl-3-acetoxy-4-(1-hydroxy-5-$^{123}$I-4-pentenyl)piperidine, N-methyl-4-acetoxy-3-(1-hydroxy-3-$^{123}$I-2-propenyl)piperidine, N-methyl-4-acetoxy-3-(1-hydroxy-5-$^{123}$I-4-pentenyl) piperidine, N-methyl-3-acetoxy-4-(1-methoxymethyloxy-3-$^{123}$I-2-propenyl)piperidine, N-methyl-3-acetoxy-4-(1-methoxymethyloxy-5-$^{123}$I-4-pentenyl)piperidine, N-methyl-4-acetoxy-3-(1-methoxymethyloxy-3-$^{123}$I-2-propenyl) piperidine, and N-methyl-4-acetoxy-3-(1-methoxymethyloxy-5-$^{123}$I-4-pentenyl)piperidine.

Examples of salts of the compounds (1), (2), (1P), and (2P) of the present invention include salts of inorganic acids such as hydrochloric acid, and salts of organic acids such as acetic acid.

Each of the compounds (1), (2), (1P), and (2P) of the present invention or salts thereof has two or three asymmetric carbon atoms in the structure, and therefore has a plurality of optical isomers. In addition, each of the optical isomers has a plurality of geometrical isomers, in accordance with the position of the halogen atom, trialkyltin group, or trialkylsilyl group at the end of R³ or $R^{3P}$. However, the present invention encompasses these optical isomers, geometrical isomers, and mixtures of these isomers.

The N-alkylpiperidine derivatives (1) or (2) of the present invention or salts thereof can be easily synthesized from the above-described precursors (1P) or (2P), or from the salts of the precursors. In this case, a non-radioactive halogen atom of the halogen-containing precursor is substituted through exchange reaction by a radioactive iodine atom, or a trialkyltin group of the trialkyltin-containing precursor or a trialkylsilyl group of the trialkylsilyl-containing precursor is directly substituted by a radioactive iodine atom, to thereby obtain the derivatives or the salts.

The precursors shown by formulas (1P) or (2P) can be produced, for example, through the following production process (A) or (B).

Production process (A)

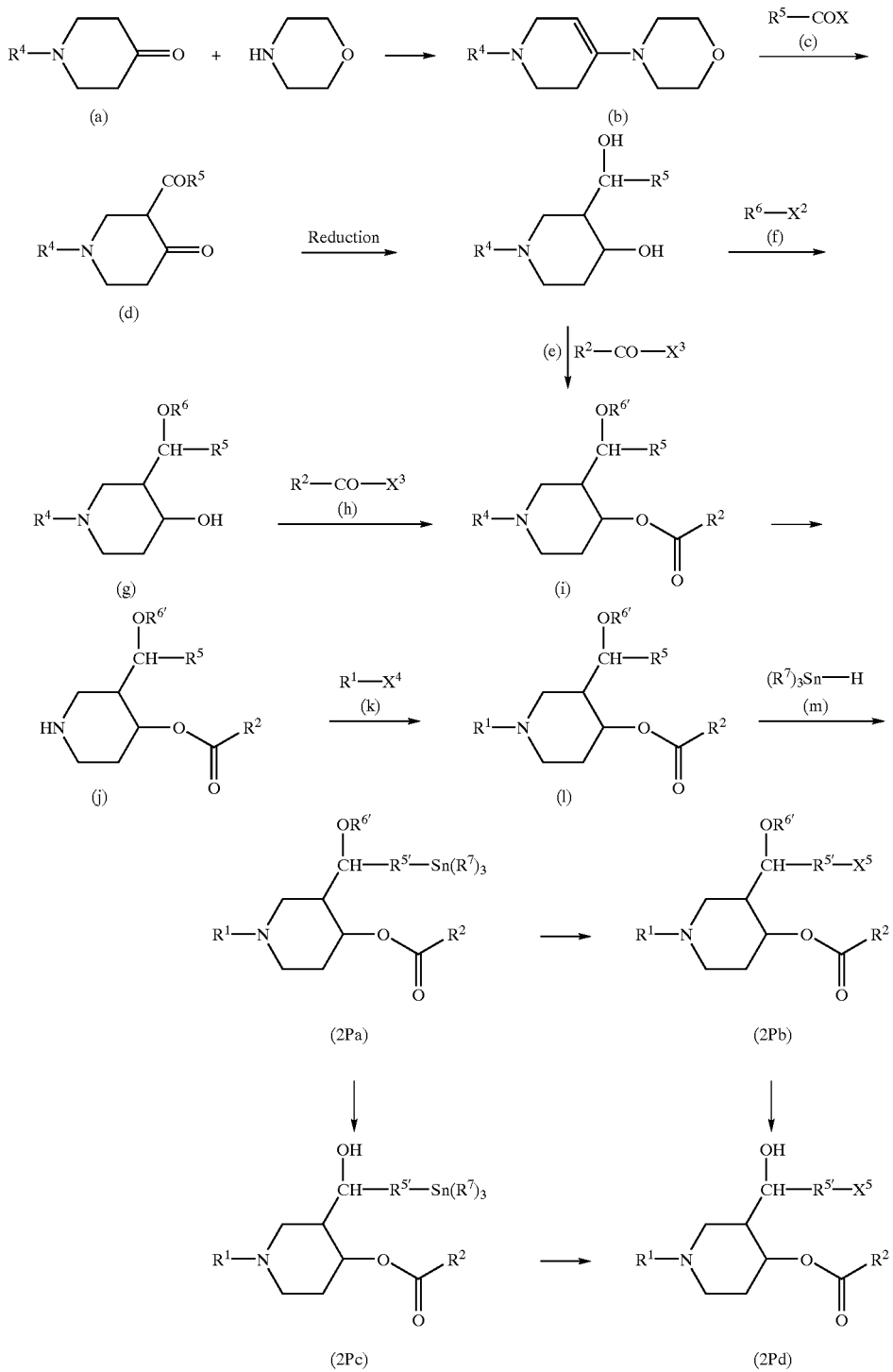

wherein $R^1$ and $R^2$ are the same as described above; $R^4$ represents an amino protective group such as a t-butoxycarbonyl group; $R^5$ represents a terminal alkenyl group; $R^{5'}$ represents a terminal alkenylene group; $R^6$ represents a lower alkyl group, a lower alkoxyalkyl group, or a lower alkoxyalkyloxyalkyl group; $R^{6'}$ represents a lower alkyl group, a lower alkoxyalkyl group, a lower alkoxyalkyloxyalkyl group, or a lower alkanoyl group; $R^7$ represents a C1–C5 alkyl group; and $X^1$, $X^2$, $X^3$, $X^4$, and $X^5$ represent halogen atoms.

An amino protective compound of 4-piperidone (a) is reacted with morpholine to form an enamine (b), and the thus-formed enamine is reacted with an alkynecarboxylic acid halide (c) to thereby obtain a diketone (d). The diketone (d) is reacted with a reducing agent such as sodium borohydride to form a diol (e), which in turn is reacted with an alkoxyalkyloxyalkyl halide, an alkoxyalkyl halide, or an alkyl halide (f) to thereby obtain a compound (g). Subsequently, the compound (g) is reacted with a carboxylic acid halide (h) to thereby obtain a compound (i). In this case, when the diol (e) is reacted with the carboxylic acid halide, the compound (i) having a lower alkanoyl group serving as $R^{6'}$ is obtained. An amino protective group of the compound (i) is eliminated to form a compound (j), and the thus-formed compound (j) is reacted with an alkyl halide (k) to thereby obtain an N-alkyl substituted compound (l). In this case, N-alkylation can be performed by condensation between the amino group and formaldehyde, followed by reduction. The N-alkyl substituted compound (l) is reacted with a trialkyltin hydride or a trialkylsilane (m) to thereby obtain the trialkyltin precursor or trialkylsilyl precursor (2Pa) of the present invention. In addition, a trialkyltin group or a trialkylsilyl group of the precursors may be substituted by a halogen atom, and $R^{6'}$ may be appropriately eliminated to thereby obtain other precursors (2Pb), (2Pc), and (2Pd).

In production process (A), for example, the compound (a) may be reacted with a trialkylsilyl halide to form a trialkylsilyloxytetrahydropyridine, which may subsequently be reacted with a dialkoxyalkane to thereby obtain the compound (g) having an alkoxy group serving as $R^6$.

Production process (B)

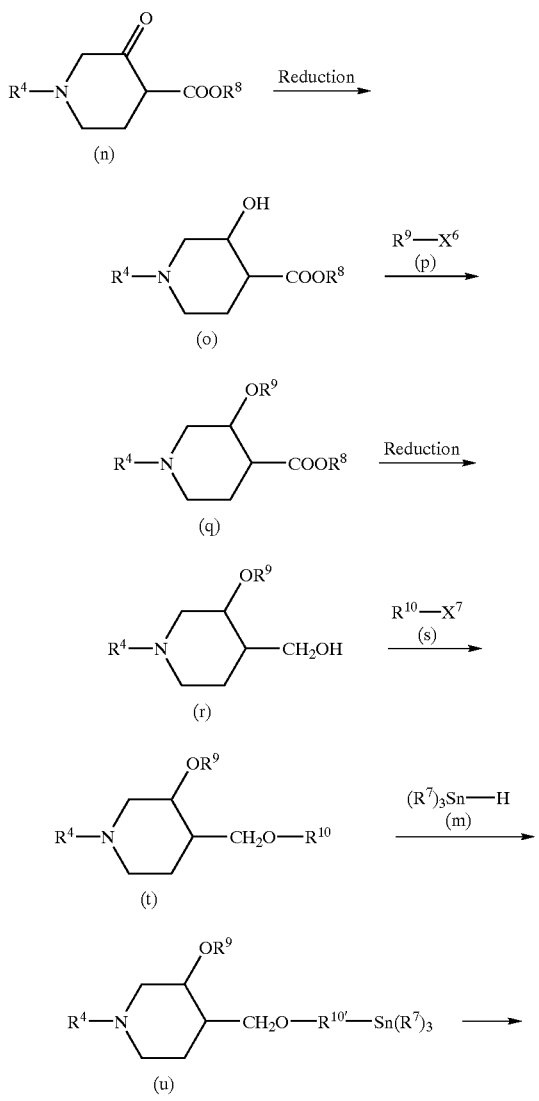

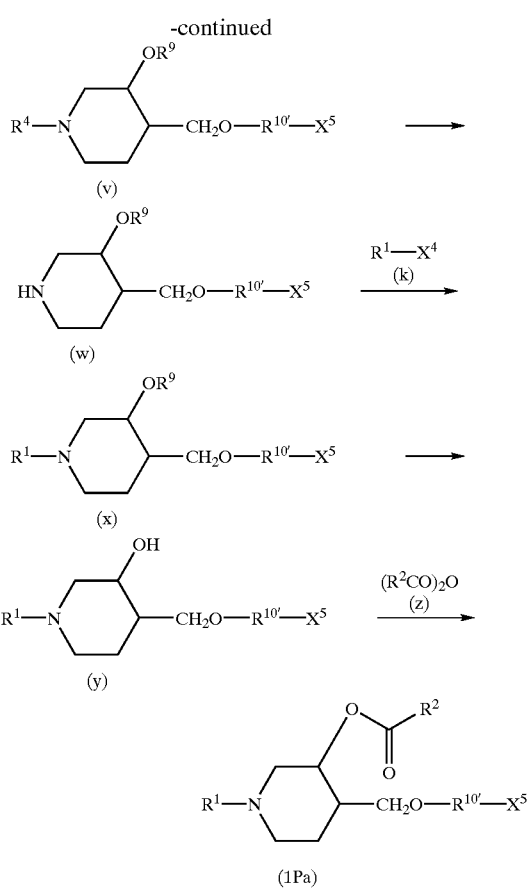

wherein $R^1$, $R^2$, $R^4$, $R^7$, $X^4$, and $X^5$ are the same as described above; $R^8$ represents a lower alkyl group; $R^9$ represents a protective group of hydroxyl group, such as a lower alkoxyalkyl group; $R^{10}$ represents a terminal alkynyl group; $R^{10'}$ represents a terminal alkenylene group; and $X^6$ and $X^7$ represent halogen atoms.

A 3-piperidone derivative (n) is reacted with a reducing agent such as sodium borohydride to thereby obtain a hydroxypiperidine derivative (o). The hydroxyl group of the thus-obtained derivative (o) is protected to form a compound (q), which is subsequently reduced to thereby obtain an alcohol (r). The thus-obtained alcohol is reacted with an alkyl halide (s) to form a compound (t), after which the compound (t) is reacted with a trialkyltin compound or a trialkylsilyl compound to thereby obtain a compound (u). The trialkyltin or trialkylsilyl group of the compound (u) is substituted by a halogen atom, and the amino group is deprotected to thereby obtain a compound (w). Subsequently, the compound (w) is reacted with an alkyl halide (k) to form the N-alkyl substituted compound (l), after which the protective group of the hydroxyl group at the 3 position is eliminated, and the thus-obtained compound is reacted with a carboxylic acid anhydride (z), to thereby obtain the halogen-containing precursor (1Pa) of the present invention.

In addition, the alcohol (r) may be oxidized to form a 4-formylpiperidine compound, and the compound may be reacted with trialkylsilylalkynyllithium to thereby obtain a 4-(α-hydroxyalkynyl) piperidine compound. The thus-obtained compound may be subjected to trialkyltin substitution, halogenation, hydrolysis, and alkanoylation in the same way as in the above production process (A) or (B), to thereby obtain the compound of formula (1P) having a hydroxyl group or a lower alkoxy group at the 1-position of $R^{3P}$.

Process (A) describes the production process of the compound of formula (2P), wherein $R^{3P}$ is an alkenyl group having a substituent at the 1-position. By the same way as in process (A), the compound of formula 1P, wherein $R^{3P}$ is an alkenyl group having a substituent at the 1-position, can be produced. Meanwhile, process (B) describes the production process of the compound of formula (1P), having an alkenyloxymethyl group serving as $R^{3P}$. By the same way as in process (B), the compound of formula (2P), having an alkenyloxymethyl group serving as $R^{3P}$, can be obtained.

As is described above, the N-alkylpiperidine derivatives (1) or (2) of the present invention or salts thereof can be easily obtained from the above-described precursors of formula (1P) and (2P) or salts thereof, wherein a non-radioactive halogen atom, a trialkyltin group, or a trialkylsilyl group of the precursors or salts thereof is substituted by a radioactive iodine atom.

Compounds (1) and (2) and the salts thereof obtained hereinabove meet the above-described four requirements as reagents for assaying central AchE activity, and are radioactive compounds emitting γ-rays at an appropriate energy level for SPECT, but each compound or each isomer has its own distinctive rate of hydrolysis. Accordingly, preferably a compound or an isomer which has high reactivity and specificity for AchE is selectively used on the occasion of application to SPECT.

Central local AchE activity can be calculated by the following method: reagents for assaying central AchE activity containing compounds (1), (2), or a salt thereof are administered; after the lapse of a predetermined time, radioactive concentration in a central local site is assayed by SPECT or autoradiography by use of a central tissue slice; while blood flow rate in the central local site is assayed; and from the relationship between these assayed values and AchE activity, central local AchE activity is calculated.

The blood flow rate in the central local site may be conveniently assayed by a reference sample method making use of $^{123}$I-labeled N-isopropyl-p-iodoamphetamine (IMP) (Lear et al., J. Cereb. Blood Flow Metabol. 2: 179–185, 1882; Kuhl et al., J. Nuc. Med. 23: 196–203,1982), and other known methods may also be employed.

In order to calculate central local AchE activity from the thus-assayed radioactive concentration and blood flow rate in the central local site, there is constructed a kinetic model incorporating distribution of the tracer in the central tissue depending on blood flow, as well as the metabolic process. The manner of incorporation of a radioactive tracer (hereinafter referred to as "tracer") into the central tissue differs depending on the blood flow rate, and the incorporated tracer in the central tissue is hydrolyzed competitively with acetylcholine by AchE into alcohols. In contrast, alcohols formed in the blood do not migrate to the central tissue. By use of a differential equation, this is expressed by the following equations (a).

$$\frac{dC_b}{dt} = F\left(C_p - \frac{1}{\lambda}C_b\right) - \frac{V_m}{K_m(1 + C_a/K_{ma}) + C_b}C_b \quad \text{(a)}$$

$$\frac{dC_m}{dt} = \frac{V_m}{K_m(1 + C_a/K_{ma}) + C_b}C_b - k_{e1}C_m$$

In the above formulas, $C_b$ represents the concentration of an unchanged tracer in the central tissue, $C_p$ represents the concentration of an unchanged tracer in the blood, F represents the blood flow rate in the central local site, and λ represents the distribution coefficient of brain blood in the equilibrium state of the tracer. F=λK holds true. K is the permeation velocity coefficient of a tracer at the blood-brain barrier (BBB). This theoretical equation for the blood-flow related incorporation of a tracer into the central tissue is the same as a theoretical equation for assaying the blood flow rate in the central local site by use of antipyrine iodide (Sakurada et al., Am. J. Physiol., 234: H59–66,1978). With regard to the incorporation into the central tissue depending on blood flow, many theoretical equations have been proposed, and a suitable one should be used depending on the employed tracer. Vm and Km represent the maximum hydrolysis rate and Michaelis constant of a tracer by AchE, respectively; $C_a$ represents concentration of free acetylcholine in the central tissue; $K_{ms}$ represents the Michaelis constant of hydrolysis of acetylcholine; $C_m$ represents concentration of alcohols in the central tissue, which alcohols are metabolites of the tracer; and $k_{el}$ represents the disappearance velocity constant of alcohols from the central tissue. Acetylcholine in the central tissue is usually accumulated in the synapse and discharged in the case of nerve conduction, and therefore, concentration of free acetylcholine $C_a$ can be qualified as nearly zero. Also, because the quantity of tracers used for the assay is trace-level, $C_b$ is far less than $K_m$ and can be ignored. Further, alcohols disappear extremely slowly in the brain, and therefore $k_{el}$ can be qualified as zero. Subsequently, the above simultaneous differential equations (a) can be rewritten as follows.

$$\frac{dC_b}{dt} = F\left(C_p - \frac{1}{\lambda}C_b\right) - K_m C_b \quad \text{(b)}$$

$$\frac{dC_m}{dt} = k_m C_b$$

In the above formulas, $k_m(=V_m/K_m)$ represents the activity of a tracer in terms of hydrolysis by AchE in the central tissue. When a tracer is injected intravenously and rapidly, transition of concentration of the unchanged tracer in the blood is expressed as $C_p = \Sigma C_{oi} \exp(-k_{ei}t)$, and the following equation (c) is derived.

$$C_b = \sum \frac{\lambda K C_{oi}}{k_{ei} - (K + k_m)}(\exp(-(K+k_m)t) - \exp(-k_{ei}t)) \quad \text{(c)}$$

$$C_m = \sum \frac{\lambda K k_m C_{oi}}{k_{ei} - (K + k_m)}\left(\frac{1 - \exp(-(K+k_m)t)}{K + k_m} - \frac{1 - \exp(-k_{ei}t)}{K_{ei}}\right)$$

If time t is sufficiently large, the exponent can be qualified as zero. In other words, concentration of an unchanged tracer in the blood and the central tissue is qualified as zero. On this occasion, solely alcohols, being metabolites, are present, and their concentration is expressed by the following equation (d).

$$C_m = \frac{\lambda K k_m}{K + k_m} \sum \frac{C_{oi}}{k_{ei}} \quad \text{(d)}$$

$$= AUC \frac{\lambda K k_m}{K + k_m}$$

Accordingly, after a tracer labeled with a radioactive element is administered intravenously, at the time point when concentration of an unchanged tracer in the blood and the central tissue becomes zero, radioactive concentration in the central tissue varies depending on AUC (area under concentration curve in the blood) of concentration of an unchanged tracer in the blood, distribution coefficient of a tracer in the brain blood, blood flow rate in the central local site, and central local AchE activity.

This is a basic equation for dynamic analysis of a tracer, but in order to obtain $k_m$, numerical values must be assayed for the AUC of concentration of an unchanged tracer in the blood and the blood flow rate in the central local site. However, because a tracer is rapidly decomposed by esterase in the blood, assaying concentration of an unchanged tracer takes time. Therefore, there was examined an assaying method in which corpus striatum having high AchE activity is employed as an internal standard. Corpus striatum is assigned an affix "s," and a region of interest in the brain is assigned an affix "o." A ratio of radioactive concentration in the central tissue is expressed by the following equation (e):

$$\frac{C_o}{C_s} = \frac{\lambda_o K_o k_{mo}}{K_o + k_{mo}} \frac{K_s + k_{ms}}{\lambda_s K_s k_{ms}} \quad (e)$$

In this case, AUCs cancel each other out. Herein, $C_o/C_s$ is replaced by Z to thereby obtain the following equation (f):

$$\frac{1}{Z} = \frac{K_s k_{ms}}{K_s + k_{ms}} \frac{\lambda_s}{\lambda_o} \left( \frac{1}{K_o} + \frac{1}{k_{mo}} \right) \quad (f)$$

In addition, the equation may be rewritten to thereby obtain the following equation (g).

$$\frac{1}{Z} = \frac{k_{ms}}{K_s + k_{ms}} \frac{\lambda_s K_s}{\lambda_o K_o} + \frac{K_s k_{ms}}{K_s + k_{ms}} \frac{\lambda_s}{\lambda_o} \frac{1}{k_{mo}} \quad (g)$$

wherein $\lambda_o K_o / \lambda_s K_s$ refers to the ratio of the blood flow rate in a region of interest to that in the corpus striatum, and $k_{mo}$ refers to hydrolysis activity of a tracer in the region of interest. Herein, $\lambda_o K_o / \lambda_s K_s$ and $k_{mo}$, are replaced by F and Y, respectively, to thereby obtain the following equation (h):

$$\frac{1}{Z} = \frac{k_{ms}}{K_s + k_{ms}} \frac{1}{F} + \frac{K_s k_{ms}}{K_s + k_{ms}} \frac{\lambda_s}{\lambda_o} \frac{1}{Y} \quad (h)$$

and the equation is solved for 1/Y, to thereby obtain the following equation (i):

$$\frac{1}{Y} = \frac{K_s + k_{ms}}{K_s k_{ms}} \frac{\lambda_o}{\lambda_s} \frac{1}{Z} - \frac{1}{K_s} \frac{\lambda_o}{\lambda_s} \frac{1}{F} \quad (i)$$

$$= \frac{\lambda_o}{\lambda_s} \left[ \left( \frac{1}{k_{ms}} + \frac{1}{K_s} \right) \frac{1}{Z} - \frac{1}{K_s} \frac{1}{F} \right]$$

In this case, Y refers to the hydrolysis activity of a tracer. Therefore, metabolic activity y of acetylcholine by AchE is obtained from the following equation (j), wherein the ratio of metabolic activity of the tracer kmo to that of acetylcholine $k_{ma}$; i.e., $k_{mo}/k_{ma}$, is replaced by $\phi$:

$$\frac{1}{y} = \phi \frac{\lambda_o}{\lambda_s} \left[ \left( \frac{1}{k_{ms}} + \frac{1}{K_s} \right) \frac{1}{Z} - \frac{1}{K_s} \frac{1}{F} \right] \quad (j)$$

$$= A \frac{1}{Z} - B \frac{1}{F}$$

In the equation, the two parameters $A = \phi(1/k_{ma} + 1/K_s)(\lambda_o/\lambda_s)$ and $B = \phi(1/K_s)(\lambda_o/\lambda_s)$ are unknown quantities. However, in animals, AchE activity y and the corpus striatum ratio of radioactive concentration in the central tissue Z can be practically measured by use of a tissue slice of brain tissue, which is obtained by punch-out.

When [$^{123}$I]IMP, serving as a tracer, is used for measurement of the blood flow rate in the central local site, the amount is represented by $C_b$/AUC ($C_b$: radioactive concentration of the central local site, AUC: concentration of unchanged IMP in the blood), and the corpus striatum ratio of blood flow in the central local site F becomes equivalent to the corpus striatum ratio of $^{123}$I concentration. Thus, the blood flow rate in the central local site can be practically measured by use of a tissue slice of the brain, which is obtained by punch-out. Therefore, in regions of the brain and corpus striatum, if the ratio of partition coefficient of tracer $\lambda_o/\lambda_s$ is almost the same in the regions, the unknown parameters A and B can be determined through application of the linear least square method to practically-measured y, Z, and F. In addition, AUC may be practically measured by use of concentration of unchanged IMP in the blood, the absolute value of blood flow in the central local site may be practically measured, and km may be practically measured by use of brain tissue obtained by punch-out. By use of these practically-measured values and the above equation (d), all parameters, including $\lambda$ and K, may be determined.

In the case of animals, since AchE activity can be practically measured in vitro, a variety of techniques are applicable to determination of parameters, and studies making use of pathologic animals are also available. Meanwhile, in the case of human subjects, mean values of parameters of a healthy human are obtained and used. In order to obtain the mean value for a healthy human, $k_m$ and $\phi$ are measured by use of the autopsied brain of a person who has perished in an accident. In addition, a tracer is administered to a healthy human and $C_m$ is measured through PET, to thereby obtain AUC. By use of these values and the blood flow rate in the central local site of the healthy human, $\lambda$ and K are obtained through equation (d). The thus-obtained values can be used for determination of the mean values of parameters A and B of the healthy human.

EXAMPLES

The present invention will next be described in more detail by way of examples, which should not be construed as limiting the invention thereto.

Example 1

(1) Water (250 ml) was added to 4-piperidone monohydrate hydrochloride salt (75 g) for dissolution, and 1 N aqueous solution of sodium hydroxide (1000 ml) was added thereto. To the solution, ditertiarybutylcarbonate (120 g) was added dropwise with stirring under cooling on ice, and the mixture was vigorously stirred for 6 hours at room temperature. The reaction mixture was subjected to extraction with ethyl acetate, and the extract was evaporated to dryness under reduced pressure to thereby yield a pale yellow solid. By recrystallization of the solid from hexane, N-t-butyloxycarbonyl-4-piperidone (3) (38.9 g) was obtained in the form of white needle-shaped crystals.

mp.: 74.4–75.2° C.

(2) To compound No. 3 (30.0 g) obtained in (1), toluene (150 ml) and morpholine (19 ml) were added, and the mixture was refluxed with heat for 20 hours in an atmosphere of nitrogen gas in a Dean-Stark reflux apparatus. After the mixture was allowed to cool, it was evaporated to dryness to thereby yield enamine (4) in the form of a pale yellow semi-solid.

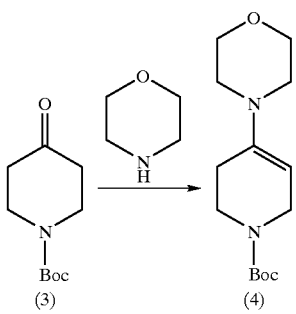

(3) Absolute dioxane (150 ml) was added to the entirety of enamine (4) obtained in (2) for dissolution, and 4-pentinoyl chloride (6.0 g) which had been synthesized from 4-pentinic acid and thionyl chloride was added dropwise thereto with stirring. The mixture was stirred with reflux with heat for 16 hours under an atmosphere of nitrogen gas. After the mixture was allowed to cool to room temperature, the resultant precipitate was separated by filtration and the filtrate was concentrated under reduced pressure to thereby obtain a reddish-brown oil. The oil was purified by silica gel chromatography (hexane:ethyl acetate=4:1) and recrystallized from hexane to thereby yield N-t-butyloxycarbonyl-3-(1-oxo-4-pentinyl)-4-piperidone (5) (6.03 g) in the form of colorless needle-shaped crystals.

mp.: 76.8–77.6° C.

High resolution mass spectrum (electron impact mode, [M–C$_4$H$_9$]$^+$): found: 222.0744 calculated: 222.0765.

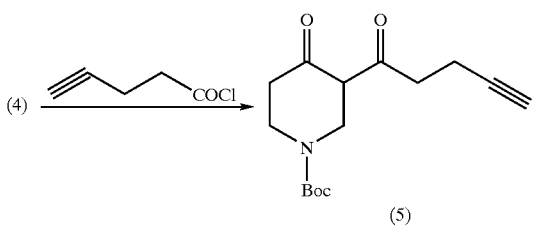

(4) Diketone (5) (5.58 g) obtained in (3) was dissolved in a 1:1 mixture (80 ml) of ethyl acetate and ethanol, and powdery sodium boron hydride (1000 mg) was added thereto portionwise with stirring at room temperature, followed by stirring for 1 hour. The reaction mixture was diluted with water and subjected to extraction with ethyl acetate. The extract was washed with water, dried over anhydrous sodium sulfate, and concentrated under reduced pressure to thereby yield N-t-butyloxycarbonyl-3-(1-hydroxy-4-pentinyl)-4-piperidinol (6) (4.82 g) in the form of a colorless oil.

High resolution mass spectrum (secondary ion mode, [M+H]$^+$): found: 284.1855. calculated: 284.1860

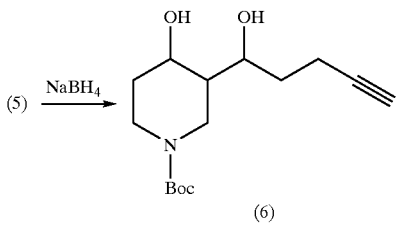

The diol (6) has 3 asymmetrical carbons and is a mixture of 8 kinds of optical isomers. These optical isomers were separated into 3 diastereomer fractions by silica gel chromatography (hexane:ethyl acetate=1:1). According to the order of elution, the eluate was collected separately as fractions (6a), (6b), and (6c), and each fraction was subjected to the following synthesis to thereby yield respective compounds which have different reactivities for AchE.

(5) To fraction (6a) (1.44 g) of diol obtained in (4), ethyl acetate (30 ml) and diisopropylethylamine (8.9 ml) were added, and further, chloromethylmethyl ether (2.0 ml) was added thereto dropwise with stirring, followed by stirring for 5 hours at room temperature. To the mixture, water was added under cooling on ice, and after 1 N hydrochloric acid (30 ml) was added dropwise thereto to thereby make the mixture acidic, the mixture was subjected to extraction with ethyl acetate. The extract was washed with water, dried over anhydrous sodium sulfate, and concentrated under reduced pressure to thereby yield a colorless oil. The oil was purified by silica gel chromatography (hexane:ethyl acetate=1:1) to thereby obtain N-t-butyloxycarbonyl-3-(1-methoxymethyloxy-4-pentinyl)-4-piperidinol (7). Further, unreacted diol (6a) was recovered from the column and again subjected to a methoxymethylation reaction and to column chromatography to thereby yield compound No. 7. Total yield of compound No. 7 was 0.60 g.

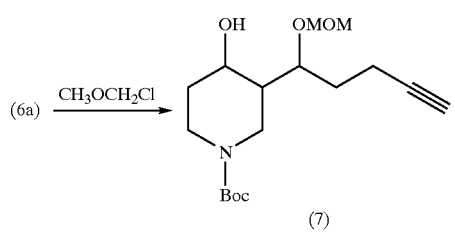

The obtained compound No. 7 is a mixture of two different optical isomers, and each enantiomer can be separated into a first isomer (7a) which elutes first and a second isomer (7b) which elutes later, by means of elution with an eluent (hexane:2-propanol=9:1) by use of Chiral HPLC (CHIRALCEL OJ column; DAICEL CHEMICAL INDUSTRIES, LTD.). By subjecting each isomer to the following synthetic method, compounds having different reactivity for AchE can be obtained.

Isomer (7a)

High resolution mass spectrum (secondary ion mode, [M+H]$^+$): found: 328.2105 calculated: 328.2122.

Angle of rotation: 90.0° $[\alpha]_D$(c=0.25%, EtOAc)

Isomer (7b)

High resolution mass spectrum (secondary ion mode, [M+H]$^+$): found: 328.2114 calculated: 328.2122.

Angle of rotation: 91.6° $[\alpha]_D$(c=0.25%, EtOAc)

(6) Isomer (7b) obtained in (5) (216 mg) was dissolved in a 1:1 mixture of hexane and methylene chloride (40 ml), and N,N-dimethylaminopyridine (806 mg) was added thereto. Acetyl chloride (235 μl) was added dropwise to the mixture with stirring, and the resultant mixture was stirred for 5 hours at room temperature. After the mixture was cooled on ice, water was added thereto, and further, 1 N hydrochloric acid (30 ml) was added dropwise to thereby make the mixture acidic. An organic phase was separated, washed with water and then with aqueous saturated brine, and dried over anhydrous sodium sulfate, followed by concentration under reduced pressure to thereby yield a colorless oil. The oil was purified by silica gel chromatography (hexane:ethyl acetate=3:1) to thereby obtain N-t-butyloxycarbonyl-3-(1-methoxymethyloxy-4-pentinyl)-4-acetoxypiperidine (8) (250 mg).

High resolution mass spectrum (electron impact mode, M+): found: 369.2160 calculated: 369.2150.

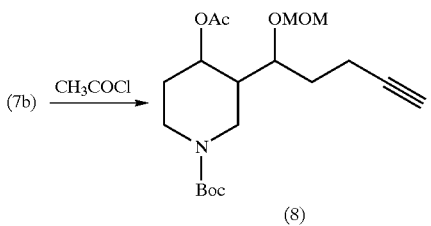

(7) Compound No. 8 (125 mg) obtained in (6) was dissolved in a 1:1 mixture of hexane and methylene chloride (20 ml), and trifluoroacetic acid (1.0 ml) was added dropwise to the solution with stirring, and further, the resultant mixture was stirred for 16 hours at room temperature. The mixture was concentrated under reduced pressure, and methylene chloride (20 ml) was added to the resultant residue. After a few drops of a concentrated ammonia water were added thereto with stirring under cooling on ice, the organic phase was separated and dried over anhydrous sodium sulfate, followed by concentration under reduced pressure to thereby yield 3-(1-methoxymethyloxy-4-pentinyl)-4-acetoxypiperidine (9) (90 mg) in the form of a colorless oil.

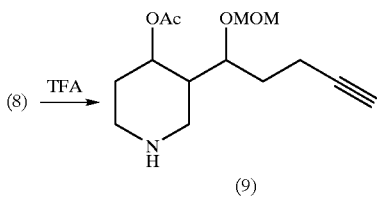

(8) Compound No. 9 (90 mg) obtained in (7) was dissolved in acetone (20 ml), methyl iodide (25 mg) was added dropwise to the solution under cooling at −80° C. with stirring, and the resultant mixture was stirred for 2 hours at room temperature. The mixture was concentrated under reduced pressure, and chloroform (15 ml) was added to the resultant residue. After a drop of aqueous concentrated solution of ammonia was added thereto under cooling on ice with stirring, the resultant mixture was dried over anhydrous sodium sulfate. The dried matter was purified by silica gel chromatography (chloroform:methanol=15:1) to thereby obtain N-methyl-3-(1-methoxymethyloxy-4-pentinyl)-4-acetoxypiperidine (10) (17 mg).

High resolution mass spectrum (electron impact mode, M+): found: 283.1818 calculated: 283.1782.

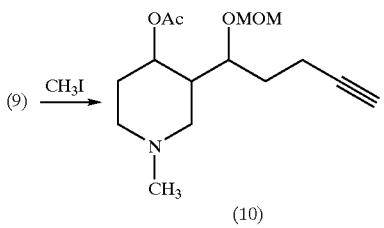

(9) Compound No. 10 (17 mg) obtained in (8) and 2,2'-azobisisobutyronitrile (5 mg) were dissolved in absolute toluene (10 ml), and hydrogenated tributyltin (100 μl) was added dropwise to the solution in an atmosphere of nitrogen gas, after which the resultant mixture was stirred for 1 hour at 85° C. The mixture was distilled off under reduced pressure, and the resultant residue was purified by silica gel chromatography (chloroform:methanol 15:1) to thereby yield N-methyl-3-(1-methoxymethyloxy-5-tributylstannyl-4-pentenyl)-4-acetoxypiperidine (11) (30 mg).

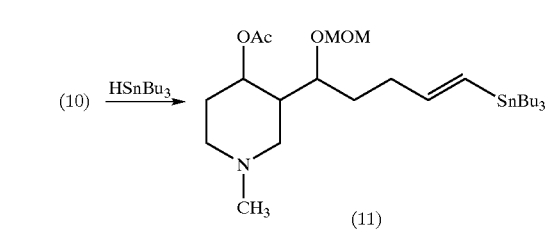

(10) Compound No. 11 (30 mg) obtained in (9) was dissolved in methylene chloride (5 ml), and a solution of N-iodosuccinimide dissolved in methylene chloride was gradually added dropwise to the mixture with stirring under cooling on ice. At a point of time when compound No. 11 disappeared, the solvent was distilled off under reduced pressure and the resultant residue was purified by silica gel chromatography (chloroform:methanol=15:1) to thereby yield N-methyl-3-(1-methoxymethyloxy-5-iodo-4-pentenyl)-4-acetoxypiperidine (12) (16 mg).

High resolution mass spectrum (electron impact mode, M+): found: 411.0908 calculated: 411.0905.

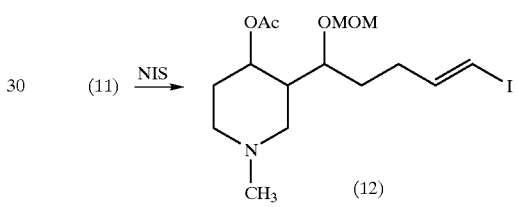

The obtained compound No. 12 is a mixture of two different geometrical isomers, and the isomers can be separated into a first isomer (12a) which elutes first and a second isomer (12b) which elutes later, by means of elution with an eluent (methanol:water:triethylamine=70:30:0.1) by use of HPLC (ODS C18 column). Each isomer has different a reactivity for AchE.

(11) Compound No. 12 (16 mg) obtained in (10) was dissolved in methylene chloride (1 ml), and after trifluoroacetic acid (3 ml) was added thereto, the mixture was allowed to stand at room temperature for 24 hours. The solvent was distilled off under reduced pressure and the resultant residue was purified by silica gel chromatography (chloroform:methanol=8:1) to thereby yield N-methyl-3-(1-hydroxy-5-iodo-4-pentenyl)-4-acetoxypiperidine (13) (13 mg).

High resolution mass spectrum (electron impact mode, M+): found: 367.0600 calculated: 367.0642.

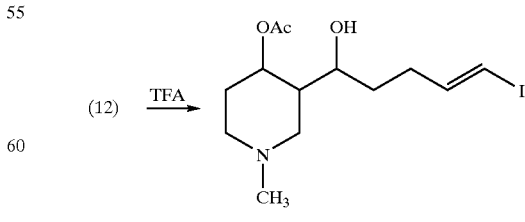

The obtained compound No. 13 is a mixture of two different geometrical isomers, and the isomers can be separated into a first isomer (13a) which elutes first and a second isomer (13b) which elutes later, by means of elution with an eluent (methanol:water:triethylamine=60:40:0.1) by use of HPLC (ODS C18 column). Each isomer has a different reactivity for AchE.

Example 2

(1) N-benzyl-4-ethoxycarbonyl-3-piperidone hydrochloride salt (15.0 g) was dissolved in a 1:1 mixture (300 ml) of ethanol and water, and 10% palladium-on-carbon (1 g) was added to the solution, followed by stirring for 12 hours in an atmosphere of hydrogen gas. The catalyst was removed by filtration and the filtrate was concentrated under reduced pressure. To the resultant residue, water (80 ml), potassium carbonate (21 g), and dioxane (100 ml) were added, and di-t-butylcarbonate (12 g) was gradually added dropwise thereto with stirring under cooling on ice, followed by stirring vigorously for 1.5 hours. The resultant mixture was diluted with water and subjected to extraction with ethyl acetate. After the extract was dried over anhydrous sodium sulfate, the solvent was distilled off under reduced pressure to thereby yield N-t-butyloxycarbonyl-4-ethoxycarbonyl-3-piperidone (14) (14.1 g).

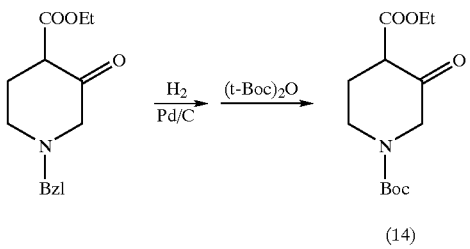

(2) Compound No. 14 (10.8 g) obtained in (1) was dissolved in methanol (50 ml), and sodium boron hydride was added thereto with stirring under cooling on ice until the raw material disappeared. The solvent was distilled off under reduced pressure and water was added to the resultant residue, which was then subjected to extraction with ethyl acetate. The extract was dried over anhydrous sodium sulfate and the solvent was distilled off under reduced pressure to thereby yield an oily matter. The oil was purified by silica gel chromatography (hexane:ethyl acetate=2:1) to thereby yield N-t-butyloxycarbonyl-3-hydroxy-4-ethoxycarbonylpiperidine (15) (6.95 g).

FAB-MS(Glycerol) [M+H]$^+$ 274

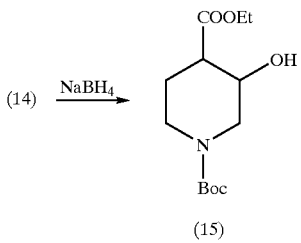

(3) Compound No. 15 (5.46 g) obtained in (2) was dissolved in ethyl acetate (50 ml), and diisopropylethylamine (10.4 ml) were added dropwise thereto with stirring and further, chloromethyl methyl ether (2.3 ml) was added dropwise thereto, followed by stirring for 48 hours at room temperature. After dilution of the mixture with water, 1 N hydrochloric acid was added thereto under cooling on ice to thereby make the mixture acidic, and the ethyl acetate layer was collected. After the ethyl acetate layer was dried over anhydrous sodium sulfate, the solvent was distilled off under reduced pressure. The resultant residue was purified by silica gel chromatography (hexane:ethyl acetate=3:1) to thereby yield N-t-butyloxycarbonyl-3-methoxymethyloxy-4-ethoxycarbonylpiperidine (16) (2.56 g) in the form of a colorless oil.

EI-MS M$^+$ 317

$^1$H-NMR(CDCl$_3$) δ: 1.27(3H, t), 1.46(9H, s), 1.61–1.72 (2H, m), 1.89–1.93(1H, m), 2.44–2.52(1H, m), 2.69–2.81 (2H, m), 3.35(3H, s), 3.78(1H, m), 3.97(1H, t), 4.17(2H, q), 4.67(2H, s)

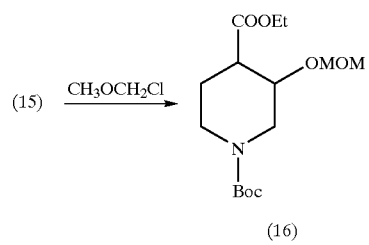

The obtained compound No. 16 has 2 asymmetric carbons and is a mixture of four different optical isomers. These optical isomers are separated into two diastereomer fractions by silica gel chromatography (hexane:ethyl acetate=5:1). According to the order of elution, the eluate was collected separately as fractions (16a) and (16b), and each fraction was subjected to the following synthesis to thereby yield respective compounds which have different reactivities for AchE.

(4) Lithium boron hydride (200 mg) was added to absolute tetrahydrofuran (30 ml), and compound No. 16a (2.23 g) obtained in (3) was added dropwise thereto, followed by reflux with heat for 4 hours. The solvent was distilled off under reduced pressure and water was added to the resultant residue, after which the mixture was subjected to extraction with ethyl acetate and the extract was dried over anhydrous sodium sulfate. The dried matter was purified by silica gel chromatography (hexane:ethyl acetate=1:1) to thereby yield N-t-butyloxycarbonyl-3-methoxymethyloxy-4-hydroxymethylpiperidine (17) (1.34 g) in the form of a colorless oil.

FAB-MS(Glycerol) [M+H]$^+$ 276

$^1$H-NMR(CDCl$_3$) δ: 1.45(9H, s), 1.58–1.82(6H, m), 2.73 (2H, bs), 3.42(3H, s), 3.59–3.70(2H, m), 3.89(1H, s), 4.59 (1H, d), 4.79(1H, d)

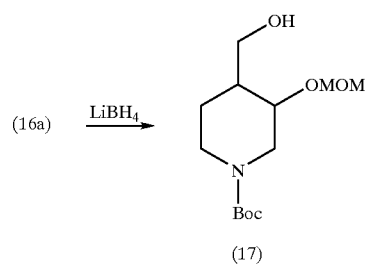

(5) Tetrahydrofuran (10 ml) was added to a 60% oil suspension of sodium hydroxide (430 mg), and compound No. 17 (987 mg) obtained in (4), which had been dissolved in tetrahydrofuran (10 ml), was added dropwise thereto, followed by stirring for 30 minutes at room temperature. Further, propargyl bromide (390 μl) was added dropwise thereto and the mixture was stirred for 16 hours at room temperature. Under cooling on ice, water was added, and then, 1 N hydrochloric acid was added to thereby make the mixture acidic. The mixture was subjected to extraction with ethyl acetate, and the extract was dried over anhydrous sodium sulfate. The dry matter was purified by silica gel chromatography (hexane:ethyl acetate=3:1) to thereby yield N-t-butyloxycarbonyl-3-methoxymethyloxy-4-propargyloxymethylpiperidine (18) (829 mg) in the form of a colorless oil.

EI-MS M⁺ 313

¹H-NMR(CDCl₃) δ: 1.45(9H, s), 1.85–1.94(1H, bs), 2.42 (2H, t), 2.71(2H, bs), 3.40(3H, s), 3.58(1H, t), 3.84(1H, s), 4.14(2H, d), 4.60(1H, d), 4.77(1H, d)

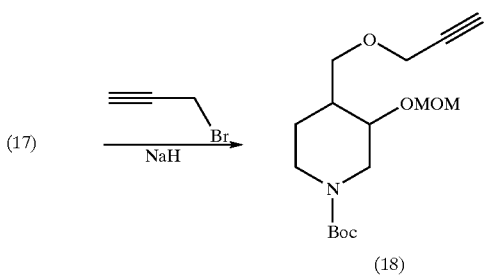

The obtained compound No. 18 is a mixture of two different geometrical isomers, and each enantiomer can be separated into a first isomer (18a) which elutes first and a second isomer (18b) which elutes later, by means of elution with an eluent (hexane:2-propanol=100:1) by use of Chiral HPLC (CHIRALCEL OJ column). By subjecting each isomer to the following synthesis, compounds having different reactivities for AchE can be obtained.

(6) Compound No. 18b (57 mg) obtained in (5) was dissolved in absolute toluene (5 ml) and under N₂ gas, 2,2'-azobisisobutyronitrile (5 mg) and subsequently, hydrogenated tributyltin (100 μl) was added, followed by stirring for 2 hours at 85–90° C. The mixture was purified by silica gel chromatography (hexane:ethyl acetate=5:1) to thereby yield N-t-butyloxycarbonyl-3-methoxymethyloxy-4-(3-tributylstannyl-2-propenyloxymethyl)piperidine (19) (57 mg) in the form of a colorless oil.

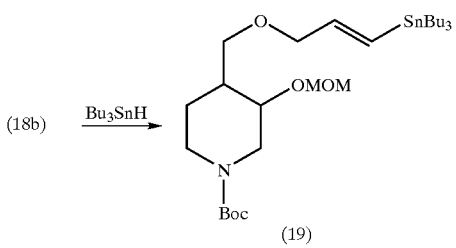

(7) Compound No. 19 (57 mg) obtained in (6) was dissolved in methylene chloride (5 ml), and N-iodosuccinimide was added thereto with stirring under cooling on ice until the raw material had disappeared. The product was purified by silica gel chromatography (hexane:ethyl acetate=3 1) to thereby yield N-t-butyloxycarbonyl-3-methoxymethyloxy-4-(3-iodo-2-propenyloxymethyl)piperidine (20) (35 mg) in the form of a colorless oil.

EI-MS M⁺ 441

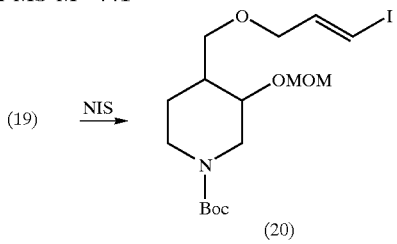

(8) Compound No. 20 (35 mg) obtained in (7) was dissolved in methylene chloride (5 ml), and trifluoroacetic acid (50 μl) was added to the solution with stirring, which was allowed to stand for 16 hours at room temperature. The mixture was concentrated under reduced pressure, and methylene chloride (5 ml) was added to the resultant residue. After a drop of an aqueous concentrated solution of ammonia was added thereto under cooling on ice with stirring, the resultant mixture was dried over anhydrous sodium sulfate and concentrated. To the resultant residue, acetone (5 ml) was added, and further, methyl iodide (5 mg) was added thereto under cooling on ice with stirring, followed by stirring for 2 hours at room temperature. The product was purified by silica gel chromatography (chloroform:methanol=15:1) to thereby yield N-methyl-3-methoxymethyloxy-4-(3-iodo-2-propenyloxymethyl) piperidine (21) (5 mg) in the form of a colorless oil.

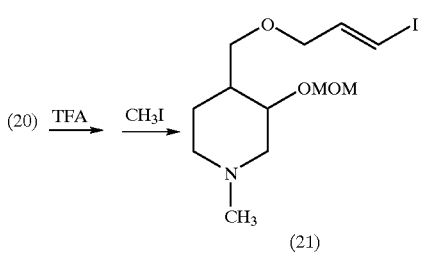

(9) To compound No. 21 (5 mg) obtained in (8), methylene chloride (0.5 ml) and trifluoroacetic acid (1 ml) were added, and the resultant mixture was allowed to stand for 16 hours at room temperature. The mixture was concentrated under reduced pressure, and to the resultant residue, pyridine (2 ml) and acetic anhydride (1 ml) were added, after which the resultant mixture was allowed to stand for 16 hours at room temperature. The product was purified by silica gel chromatography (chloroform:methanol=15:1) to thereby yield N-methyl-3-acetoxy-4-(3-iodo-2-propenyloxymethyl) piperidine (22) (5 mg) in the form of a colorless oil.

EI-MS M⁺ 353

¹H-NMR(CDCl₃) δ: 1.53–1.62(1H, m), 1.70–1.79(1H, bs), 1.92–2.10(3H, bs), 2.06(3H, s), 2.35(3H, s), 2.84–2.86 (1H, m), 3.03–3.07(1H, m), 3.28–3.32(1H, m), 3.44–3.48 (1H, m), 3.85–3.87(2H, m), 4.81–4.86(1H, m), 6.36(1H, d), 6.58(1H, m)

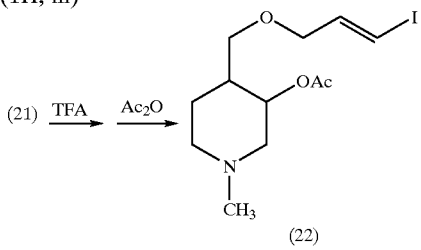

Example 3

(1) Compound No. 6a (2.83 g) obtained in Example 1 (4) and N,N-diisopropylethylamine (8.7 ml) were dissolved in methylene chloride (50 ml), and 2-methoxyethoxymethyl chloride (2.85 ml) was added dropwise thereto, followed by stirring for 12 hours at room temperature. After completion of the reaction, water was added thereto under cooling on ice, and 1 N hydrochloric acid was added dropwise thereto to thereby make the mixture acidic. Subsequently, the organic phase was removed and the water phase was subjected to extraction with methylene chloride. The extract was combined with the organic phase and washed with water and aqueous saturated brine. After the mixture was dried over anhydrous sodium sulfate, the solvent was distilled off under reduced pressure. The resultant residue was purified by silica gel chromatography (methylene chloride:methanol=100:1) to thereby yield 1-t-butoxycarbonyl-3-[1-(2-methoxyethoxy)-methoxy-4-pentinyl]-4-piperidinol (23) (2.12 g) in the form of a colorless oil.

$^1$H-NMR(CDCl$_3$) δ: 1.46(9H, s), 1.53–1.62(2H, m), 1.74–1.79(1H, m), 1.94(1H, s), 2.34–2.37(2H, m), 3.09–3.20(2H, m), 3.40(3H, s), 3.56–3.58(2H, m), 3.69–3.79(2H, m), 3.92–3.98(2H, bs), 4.11(1H, d), 4.77(1H, d), 4.87(1H, d)

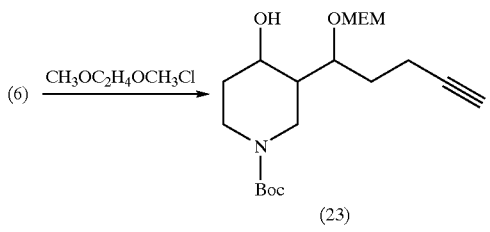

(2) Compound No. 23 (2.02 g) obtained in (1) and 4-dimethylaminopyridine (2.93 g) were dissolved in methylene chloride (50 ml), and acetyl chloride (0.85 ml) was added dropwise thereto under cooling on ice, followed by stirring for 2 hours at room temperature. After completion of the reaction, water was added thereto under cooling on ice, and 1 N hydrochloric acid was added dropwise thereto to thereby neutralize the mixture. Subsequently, the organic phase was removed, and the water phase was subjected to extraction with methylene chloride. The extract was combined with the organic phase and washed with water and aqueous saturated brine. After the mixture was dried over anhydrous sodium sulfate, the solvent was distilled off under reduced pressure. The resultant residue was purified by silica gel chromatography (n-hexane:ethyl acetate=3:1) to thereby yield N-t-butyloxycarbonyl-3-[1-(2-methoxyethoxy)-methoxy-4-pentinyl]-4-acetoxypiperidine (24) (1.87 g) in the form of a colorless oil.

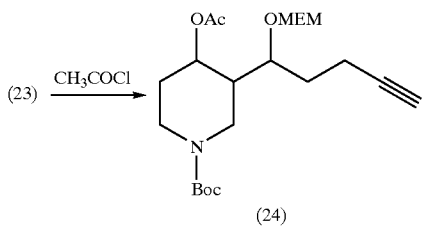

(3) Compound No. 24 (300 mg) obtained in (2) was dissolved in methylene chloride (20 ml), and trifluoroacetic acid (1.67 ml) in methylene chloride (5 ml) was added dropwise to the solution, followed by stirring for 30 minutes at room temperature. The reaction mixture was concentrated, and the resultant residue was dissolved in chloroform (10 ml). After the solution was washed with aqueous saturated sodium hydrogencarbonate and the organic phase was dried over anhydrous sodium sulfate, the solvent was distilled off under reduced pressure. The obtained residue in the form of a pale yellow oil was suspended in a mixed solvent of acetonitrile (5 ml), water (3 ml), and methanol (5 ml). To the suspension, a 37 wt. % solution (330 μl) of formaldehyde was added, and further, sodium cyanoborohydride (150 mg) was added thereto under cooling on ice, followed by stirring for 15 hours at room temperature. The reaction mixture was concentrated, and water (10 ml) was added to the resultant residue. Acetic acid was added dropwise thereto to thereby adjust the pH of the mixture to 3, and then the mixture was subjected to extraction with chloroform.

The organic phase was washed with aqueous saturated sodium hydrogencarbonate and dried over anhydrous sodium sulfate, and then the solvent was distilled off under reduced pressure. The obtained residue was purified by silica gel chromatography (methylene chloride:methanol=15:1) to thereby yield N-methyl-3-[1-(2-methoxyethoxy)-methoxy-4-pentinyl]-4-acetoxypiperidine (25) (130 mg) in the form of a colorless oil.

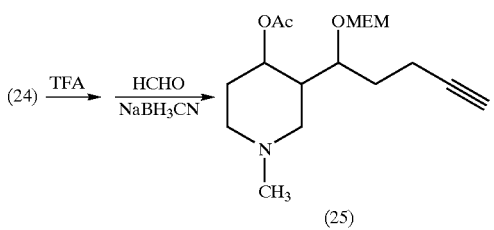

(4) Compound No. 25 (120 mg) obtained in (3) and hydrogenated tri-n-butyl tin (148 μl) were dissolved in absolute toluene (5 ml), and tetrakis(triphenylphosphine) palladium (21 mg) was added to the solution at 0° C. under argon, followed by stirring for 1 hour at room temperature. The mixture was concentrated, and the resultant residue was subjected to silica gel chromatography (methylene chloride:methanol=20:1) to thereby obtain a fraction of interest. The fraction was purified by NH silica gel chromatography (n-hexane:ethyl acetate=3:1) to thereby yield N-methyl-3-[1-(2-methoxyethoxy)methoxy-5-tributylstannyl-4-pentenyl]-4-acetoxypiperidine (26) (160 mg) in the form of a pale yellow oil.

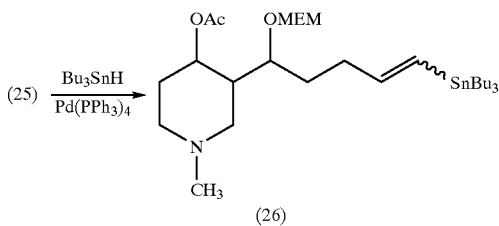

The obtained compound No. 26 is a mixture of two different geometrical isomers, and the isomers can be separated into a first isomer (26a) which elutes first and the other isomer (26b) which elutes later, by means of elution with an eluent (methanol:water:triethylamine=90:10:0.2) by use of HPLC (ODS C18 column). Each isomer has a different reactivity for AchE.

(5) Compound No. 26b (43 mg) obtained in (4) was dissolved in methylene chloride (3 ml), and N-iodosuccinimide (25 mg) dissolved in methylene chloride (3 ml) was gradually added dropwise to the mixture at 0° C., followed by stirring for 5 minutes at the same temperature. The solvent was distilled off under reduced pressure, and the resultant residue was purified by silica gel chromatography (methylene chloride:methanol=10:1) to thereby yield N-methyl-3-[1-(2-methoxyethoxy)methoxy-5-trans-iodo-4-pentenyl]-4-acetoxypiperidine (27) (19 mg) in the form of a colorless oil.

$^1$H-NMR(CDCl$_3$) δ: 1.59–1.68(2H, m), 1.81–1.97(2H, m), 2.06(3H, s), 2.08–2.23(5H, m), 2.28(3H, s) 2.52–2.60 (2H, m), 3.40(3H, s), 3.54(2H, t), 3.66–3.76(2H, m), 3.86 (1H, s), 4.67(1H, d), 4.80(1H, d), 5.02–5.08(1H, m), 6.02 (1H, d), 6.47–6.54(1H, m)

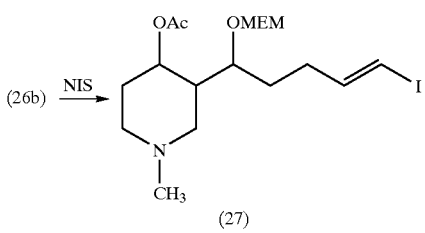

Example 4

(1) Compound No. 6a (2.27 g) and 4-dimethylaminopiperidine (5.86 g) were dissolved in methylene chloride (100 ml), and acetyl chloride (1.71 ml) was added dropwise thereto under cooling on ice, followed by stirring for 2 hours at room temperature. After completion of the reaction, water was added thereto under cooling on ice, and 1 N hydrochloric acid was added dropwise thereto for neutralization of the mixture. Subsequently, the organic phase was removed and the water phase was subjected to extraction with methylene chloride. The extract was combined with the organic phase, and the mixture was washed with water and aqueous saturated brine. After the mixture was dried over anhydrous sodium sulfate, the solvent was distilled off under reduced pressure. The resultant residue was purified by silica gel chromatography (n-hexane:ethyl acetate=3:1) to thereby yield N-t-butyloxycarbonyl-3-(1-acetoxy-4-pentinyl)-4-acetoxypiperidine (28) (2.05 g) in the form of a colorless oil.

$^1$H-NMR(CDCl$_3$) δ: 1.46(9H, s), 1.62–1.78(2H, m), 1.84–1.95(4H, m), 2.09(3H, s), 2.11(3H, s), 2.16–2.22(2H, m), 2.92(2H, bs), 3.90(2H, bs), 5.01(1H, bs), 5.20(1H, s)

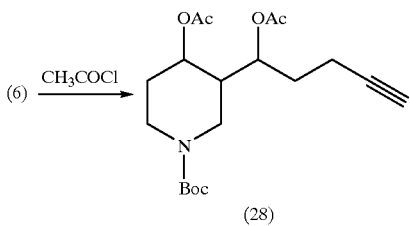

(2) Compound No. 28 (1.8 g) obtained in (1) was dissolved in chloroform (100 ml), and trifluoroacetic acid (15.1 ml) was added dropwise to the solution under cooling on ice, followed by stirring for 30 minutes at room temperature. The reaction mixture was concentrated, and the resultant residue was again dissolved in chloroform (100 ml). After the solution was washed with aqueous saturated sodium hydrogencarbonate and the organic phase was dried over anhydrous sodium sulfate, the solvent was distilled off under reduced pressure. The obtained residue in the form of a pale yellow oil was suspended in a mixed solvent of acetonitrile (20 ml), water (10 ml), and methanol (20 ml). To the suspension, a 37 wt. % solution (2.25 ml) of formaldehyde was added, and further, sodium cyanoborohydride (1.0 g) was added thereto under cooling on ice, followed by stirring for 16 hours at room temperature. The reaction mixture was concentrated, and water (30 ml) was added to the resultant residue. Acetic acid was added dropwise thereto to thereby adjust the pH of the mixture to 3, and then the mixture was subjected to extraction with chloroform. After the organic phase was dried over anhydrous sodium sulfate, the solvent was distilled off under reduced pressure. The obtained residue was purified by silica gel chromatography (methylene chloride:methanol=20:1) to thereby yield N-methyl-3-(1-acetoxy-4-pentinyl)-4-acetoxypiperidine (29) (570 mg) in the form of a white amorphous powder.

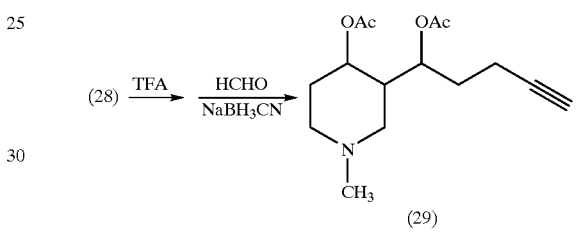

(3) To a solution of compound No. 29 (282 mg) obtained in (2) and hydrogenated tri-n-butyltin (404 μl) in absolute toluene (10 ml), tetrakis(triphenylphosphine) palladium (58 mg) was added at 0° C. under argon gas and the resultant mixture was stirred for 1 hour at room temperature. The reaction mixture was concentrated, and the resultant residue was subjected to silica gel chromatography (methylene chloride:methanol=20:1) to thereby obtain a fraction of interest. The fraction was purified by NH silica gel chromatography (n-hexane:ethyl acetate=3:1) to thereby yield N-methyl-3-(1-acetoxy-5-tributylstannyl-4-pentenyl)-4-acetoxypiperidine (30) (460 mg) in the form of a pale yellow oil.

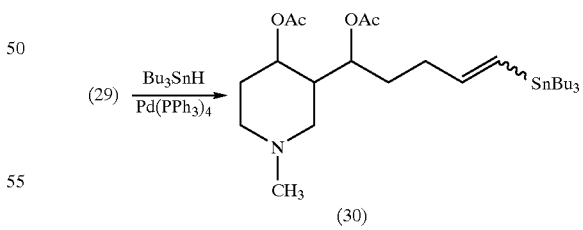

The obtained compound No. 30 is a mixture of two different geometrical isomers, and the isomers can be separated into a first isomer (30a) which elutes first and a second isomer (30b) which elutes later, by means of elution with an eluent (methanol:water:triethylamine=90:10:0.2) by HPLC (ODS C18 column). Each isomer has a different reactivity for AchE.

(4) Compound No. 30b (115 mg) obtained in (3) was dissolved in methylene chloride (3 ml), and N-iodosuccinimide (54 mg) dissolved in methylene chloride (5 ml) was gradually added dropwise to the mixture at 0° C., followed by stirring for 5 minutes at the same temperature. The solvent was distilled off under reduced pressure, and the resultant residue was purified by silica gel chromatography (methylene chloride:methanol=10:1) to thereby yield N-methyl-3-(1-acetoxy-5-trans-iodo-4-pentenyl)-4-acetoxypiperidine (31) (62 mg) in the form of pale yellow needle-shaped crystals.

$^1$H-NMR(CDCl$_3$) δ: 1.53–1.62(1H, m), 1.68–1.80(2H, m), 1.86–2.15(6H, m), 2.07(3H, s), 2.10(3H, s), 2.30(3H, s), 2.59–2.63(2H, m), 4.85–4.90(1H, m), 5.06(1H, d), 6.02(1H, d), 6.42–6.49(1H, m)

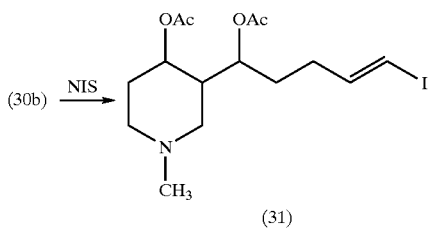

Example 5

(1) To a solution of diisopropylamine (15.2 ml) in absolute tetrahydrofuran (200 ml), a 1.6 M solution of n-butyl lithium in n-hexane (60 ml) was added dropwise at -78° C. under argon gas. The temperature was raised to 0° C. and the mixture was stirred for 30 minutes. Again the temperature was lowered to -78° C., and N-t-butyloxycarbonyl-4-piperidone (3) (17.9 g) dissolved in absolute tetrahydrofuran (30 ml) was added dropwise to the mixture, followed by stirring for 1 hour at the same temperature. Chlorotrimethylsilane (17.2 ml) was added thereto, and the resultant mixture was stirred for 1 hour at room temperature. The reaction mixture was concentrated and water was added to the resultant residue, followed by extraction with diethyl ether. The organic phase was washed with water and aqueous saturated brine, and dried over anhydrous sodium sulfate. The solvent was distilled off under reduced pressure, and the resultant residue was purified by vacuum distillation to thereby yield N-t-butyloxycarbonyl-4-trimethylsilyloxy-1,2,3,6-tetrahydropyridine (32) (14.6 g) in the form of a colorless oil.

bp$_{0.2}$ 107° C.

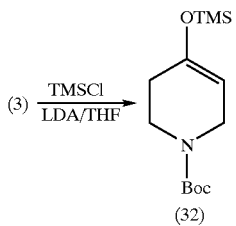

(2) Compound No. 32 (8.14 g) obtained in (1) and 5,5-dimethoxy-1-pentyne (33) (4.23 g) were dissolved in absolute methylene chloride (200 ml), and to the solution, a solution of trimethylsilyltrifluoromethane sulfonate (270 μl) in absolute methylene chloride (15 ml) was added dropwise at -78° C. under argon gas, followed by stirring for 16 hours at the same temperature. Water (20 ml) was added thereto to thereby return the reaction mixture to room temperature, and the organic phase was removed. Subsequently, the water phase was subjected to extraction with methylene chloride, and the extract was combined with the organic phase and washed with aqueous saturated sodium hydrogencarbonate, water, and aqueous saturated brine. After the mixture was dried over anhydrous sodium sulfate, the solvent was distilled off under reduced pressure. The resultant residue was purified by silica gel chromatography (n-hexane:ethyl acetate=5:1) to thereby yield N-t-butyloxycarbonyl-3-(1-mthoxy-4-pentinyl)-4-piperidone (34) (1.34 g) in the form of a colorless oil.

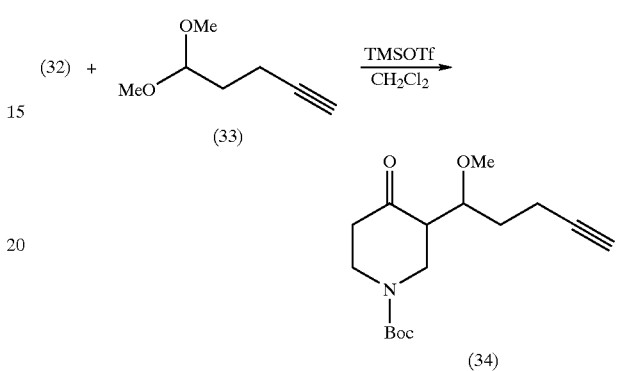

(3) Compound No. 34 (3.4 g) obtained in (2) was dissolved in a mixed solvent of ethyl acetate (50 ml) and ethanol (50 ml), and sodium borohydride (250 mg) was added to the solution, followed by stirring for 30 minutes at room temperature. The reaction mixture was diluted with water and subjected to extraction with ethyl acetate. The organic phase was washed with water and aqueous saturated brine, dried over anhydrous sodium sulfate, and concentrated under reduced pressure. The obtained residue was purified by silica gel column chromatography (n-hexane:ethyl acetate=2:1) to thereby yield N-t-butyloxycarbonyl-3-(1-methoxy-4-pentinyl)-4-piperidinol (35) (1.42 g) in the form of a colorless oil.

$^1$H-NMR(CDCl$_3$) δ: 1.46(9H, s), 1.57–1.77(5H, m), 1.91–1.99(2H, m), 2.23–2.37(3H, m), 3.14(2H, bs), 3.40 (3H, s), 3.60(1H, bs), 3.94(1H, bs), 4.17(1H, s)

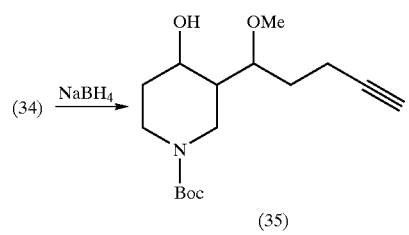

(4) Compound No. 35 (1.16 g) obtained in (3) and 4-(N,N-dimethylamino)pyridine (2.38 g) were dissolved in methylene chloride (50 ml), and acetyl chloride (0.55 ml) in methylene chloride (5 ml) was added dropwise thereto under cooling on ice, followed by stirring for 2 hours at room temperature. After completion of the reaction, water was added thereto under cooling on ice, and 1 N hydrochloric acid was added dropwise thereto for neutralization of the mixture. Subsequently, the organic phase was removed, and the water phase was subjected to extraction with methylene chloride. The extract was combined with the organic phase, and the mixture was washed with water and aqueous saturated brine. After the mixture was dried over anhydrous sodium sulfate, the solvent was distilled off under reduced pressure. The resultant residue was purified by silica gel chromatography (n-hexane:ethyl acetate=4:1) to thereby yield N-t-butyloxycarbonyl-3-(1-methoxy-4-pentinyl)-4-acetoxypiperidine (36) (1.17 g) in the form of a colorless oil.

(n-hexane:ethyl acetate=2:1) to thereby yield N-methyl-3-(1-methoxy-5-tributylstannyl-4-pentenyl)-4-acetoxypiperidine (38) (510 mg) in the form of a pale yellow oil.

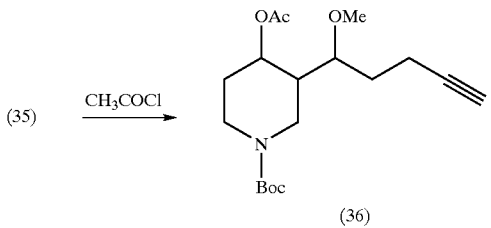

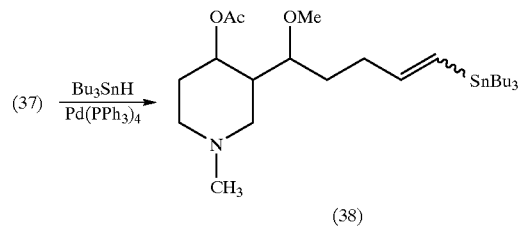

(5) Compound No. 36 (1.15 g) obtained in (4) was dissolved in chloroform (50 ml), and trifluoroacetic acid (7.70 ml) was added dropwise to the solution under cooling on ice, followed by stirring for 2 hours at room temperature. The reaction mixture was concentrated, and the resultant residue was again dissolved in chloroform (100 ml). After the solution was washed with aqueous saturated sodium hydrogencarbonate and the organic phase was dried over anhydrous sodium sulfate, the solvent was distilled off under reduced pressure. The obtained residue in the form of a pale yellow oil was suspended in a mixed solvent of acetonitrile (20 ml), water (10 ml), and methanol (20 ml). To the suspension, 37 wt. % solution (1.50 ml) of formaldehyde was added and further, sodium cyanoborohydride (660 mg) was added thereto under cooling on ice, followed by stirring for 18 hours at room temperature. The reaction mixture was concentrated, and water (30 ml) was added to the resultant residue. Acetic acid was added dropwise thereto to thereby adjust the pH of the mixture to 3, and then the resultant mixture was subjected to extraction with chloroform. The organic phase was washed with aqueous saturated sodium hydrogencarbonate and dried over anhydrous sodium sulfate, and then the solvent was distilled off under reduced pressure. The obtained residue was purified by silica gel chromatography (methylene chloride:methanol=15:1) to thereby yield N-methyl-3-(1-methoxy-4-pentenyl)-4-acetoxypiperidine (37) (340 mg) in the form of a white amorphous powder.

The obtained compound No. 38 is a mixture of two different geometrical isomers, and the isomers can be separated into a first isomer (38a) which elutes first and a second isomer (38b) which elutes later, by means of elution with an eluent (methanol:water:triethylamine=90:10:0.2) by use of HPLC (ODS C18 column). Each isomer has a different reactivity for AchE.

(7) Compound No. 38b (90 mg) obtained in (6) was dissolved in methylene chloride (3 ml), and N-iodosuccinimide (45 mg) dissolved in methylene chloride (5 ml) was gradually added dropwise to the mixture at 0° C., followed by stirring for 5 minutes at the same temperature. The solvent was distilled off under reduced pressure, and the resultant residue was purified by silica gel column chromatography (methylene chloride:methanol=10:1) to thereby yield N-methyl-3-(1-methoxy-5-trans-iodo-4-pentenyl)-4-acetoxypiperidine (39) (41 mg) in the form of pale yellow needle-shaped crystals.

$^1$H-NMR(CDCl$_3$) δ: 1.44–1.53(1H, m), 1.63–1.81(2H, m), 1.86–1.96(2H, m), 2.08(3H, s), 2.09–2.17(4H, m), 2.32 (3H, s), 2.62–2.65(1H, m), 2.90–2.94(1H, m), 3.06–3.11 (1H, m), 3.29(3H, s), 5.02(1H, d), 6.02(1H, d), 6.48–6.53 (1H, d),

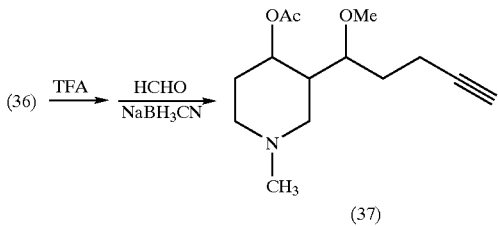

(6) To a solution of compound No. 37 (300 mg) obtained in (5) and hydrogenated tri-n-butyltin (478 µl) in absolute toluene (10 ml), tetrakis(triphenylphosphine) palladium (68 mg) was added at 0° C. under argon gas, followed by stirring for 1 hour at room temperature. The reaction mixture was concentrated, and the resultant residue was subjected to silica gel chromatography (methylene chloride:methanol= 20:1) to thereby obtain a fraction of interest. The fraction was purified by NH silica gel chromatography Example 6

(1) Absolute methylene chloride (75 ml) was added to pyridinium chlorochromate (2.61 g), and to the solution, a solution of the compound No. 17 (2.22 g) obtained in Example 2 (4) in absolute methylene chloride (25 ml) was added with stirring, followed by stirring for 3 hours. Insoluble matter was removed by filtration, and the filtrate was evaporated to dryness. The resultant residue was purified by silica gel chromatography (n-hexane:ethyl acetate= 1:1) to thereby yield N-t-butyloxycarbonyl-3-methoxymethyloxy-4-formylpiperidine (40) (1.63 g) in the form of a colorless oil.

1H-NMR(CDCl₃) δ: 1.46(9H, s), 1.48–1.59(3H, bs), 1.87 (1H, d), 2.51(1H, bs), 2.81–2.88(1H, bs), 3.36(3H, s), 3.78–3.84(1H, m), 3.96(1H, d), 4.65(1H, d), 4.74(1H, d), 9.75(1H, d)

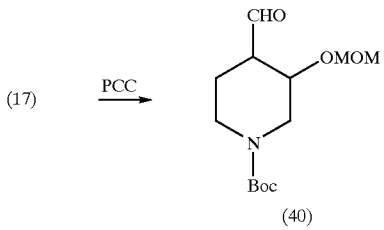

(2) Absolute tetrahydrofuran (25 ml) was added to trimethylsilylacetylene (2.1 ml), and to the mixture, a solution (7.5 ml) of 1.6 M n-butyllithium in hexane was added dropwise with stirring in the temperature range of −5° C. to 0° C. in an atmosphere of nitrogen gas, followed by stirring for 10 minutes. The resultant mixture was added dropwise to a solution of compound No. 40 (1.63 g) obtained in (1) in absolute tetrahydrofuran (10 ml) with stirring in the temperature range of −5° C. to 0° C. in an atmosphere of nitrogen gas, followed by stirring for 1 hour and another round of stirring for 1 hour at room temperature. To the reaction mixture, a 10% aqueous solution (20 ml) of ammonium chloride was added, and the resultant mixture was diluted with water and subjected to extraction with ethyl acetate. After the organic phase was washed with water and dried over anhydrous sodium sulfate, the solvent was distilled off under reduced pressure. To the residue, methanol (30 ml) and an aqueous 5 N potassium hydroxide solution (3 ml) were added, and the resultant mixture was heated at 60° C. for 30 minutes. The reaction mixture was concentrated, and to the resultant residue, 10% aqueous solution (20 ml) of ammonium chloride was added. The resultant solution was diluted with water and subjected to extraction with ethyl acetate. The organic phase was washed with water and dried over anhydrous sodium sulfate. The solvent was distilled off under reduced pressure. To the residue were added methanol (30 ml) and an aqueous 5 N potassium hydroxide solution, and the mixture was heated for 30 minutes at 60° C. The reaction product was concentrated, and 10% aqueous ammonium chloride solution (20 ml) was added to the residue, followed by dilution with water and extraction with ethyl acetate. The organic phase was washed with water, dried over anhydrous sodium sulfate, and purified by silica gel column chromatography (n-hexane:ethyl acetate=3:1) to thereby yield N-t-butyloxycarbonyl-3-methoxymethyloxy-4-(1-hydroxypropargyl)piperidine (41). The obtained compound was separated into a first isomer (41a) which elutes first and a second isomer (41b) which elutes later, by means of elution with an eluent (hexane:2-propanol =100:3) by use of Chiral HPLC (CHIRALCEL 0J column). The yield of each isomer was 220 mg. FAB-MS (3-Nitrobenzyl alcohol) [M+H]⁺ 300

¹H-NMR(CDCl₃) δ: 1.46(9H, s), 1.50–1.59(2H, m), 1.75–1.84(2H, m), 2.49(1H, d), 2.54(1H, bs), 2.64–2.67(1H, bs), 3.43(3H, s), 3.69–3.76(1H, m), 4.11–4.16(1H, bs), 4.59 (1H, bs), 4.73–4.77(2H, dd)

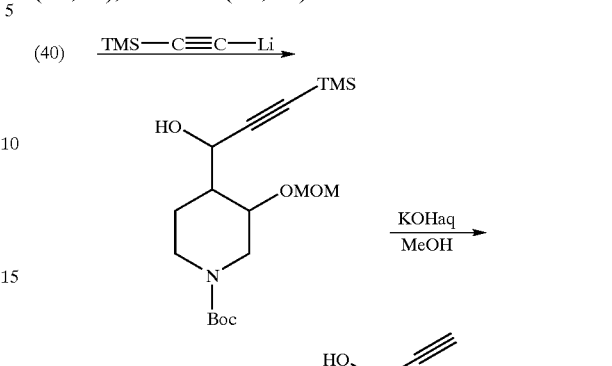

(3) To compound No. 41b (50 mg) obtained in (2), absolute pyridine (500 μl) and acetic anhydride (250 μl) were added, and the resultant mixture was allowed to stand for 16 hours at room temperature. The reaction mixture was purified by silica gel chromatography (n-hexane:ethyl acetate=3:1) to thereby yield N-t-butyloxycarbonyl-3-methoxymethyloxy-4-(1-acetoxypropargyl)piperidine (42) (56 mg) in the form of an oil.

¹H-NMR(CDCl₃) δ: 1.47(9H, s), 1.61(1H, bs), 1.78–1.84 (1H, bs), 2.01–2.06(1H, bs), 2.09(3H, s), 2.45(1H, d), 2.49–2.52(1H, bs), 2.65–2.71(1H, bs), 3.34(3H, s), 3.37(1H, m), 4.13(1H, bs), 4.39(1H, bs), 4.55(1H, d), 4.68(1H, d), 5.69(1H, d)

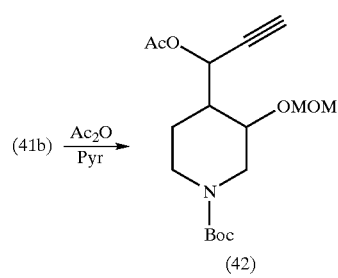

(4) To compound No. 42 (56 mg) obtained in (3), absolute toluene (3 ml), 2,2'-azobisisobutyronitrile (2 mg), and hydrogenated tributyltin (200 μl) were added, and the resultant mixture was stirred for 1 hour at 85° C. in an atmosphere of nitrogen gas. The reaction mixture was purified by silica gel chromatography (n-hexane:ethyl acetate=5:1) to thereby yield N-t-butyloxycarbonyl-3-methoxymethyloxy-4-(1-acetoxy-3-tributylstannyl-2-propenyl)piperidine (43) (87 mg) in the form of an oil.

¹H-NMR(CDCl₃) δ: 0.88(15H, t), 1.25–1.34(6H, m), 1.43–1.52(7H, m), 1.46(9H, s), 1.63–1.71(2H, bs), 2.09(3H, s), 2.55–2.65(2H, bs), 3.31–3.35(1H, bs), 3.36(3H, s), 4.06(1H, bs), 4.38(1H, bs), 4.58(1H, d), 4.70(1H, d), 5.64(1H, bs), 5.83(1H, dd), 6.08(1H, dd)

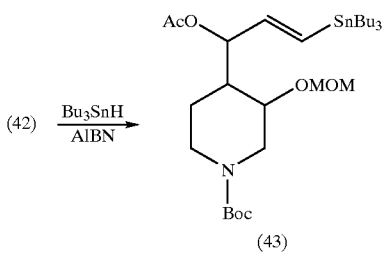

(5) Compound No. 43 (87 mg) obtained in (4) was dissolved in methylene chloride (3 ml), and a solution of N-iodosuccinimide in methylene chloride was added dropwise to the solution with stirring under cooling on ice. At a point in time when the compound No. 43 had disappeared, the solvent was distilled off under reduced pressure and the resultant residue was purified by silica gel chromatography (n-hexane:ethyl acetate=5:1) to thereby yield N-t-butyloxycarbonyl-3-methoxymethyloxy-4-(1-acetoxy-3-iodo-2-propenyl)piperidine (44) (48 mg) in the form of an oil.

¹H-NMR(CDCl₃) δ: 1.46(9H, s), 1.60–1.73(2H, m), 2.08(3H, s), 2.52–2.66(2H, bs), 3.27–3.28(1H, bs), 3.35(3H, s), 4.08(1H, s), 4.55(1H, d), 4.68(1H, d), 5.60(1H, d), 6.40(1H, dd), 6.51(1H, d)

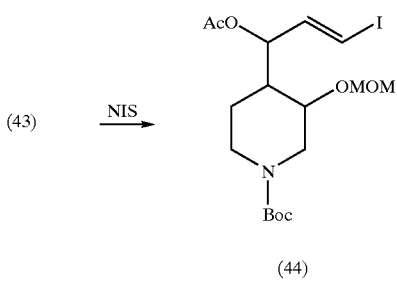

(6) To compound No. 44 (48 mg) obtained in (5), methylene chloride (3 ml) and trifluoroacetic acid (0.1 ml) were added, and the resultant mixture was allowed to stand for 16 hours at room temperature. The mixture was concentrated under reduced pressure, and to the resultant residue, methylene chloride (5 ml) was added. After one drop of concentrated ammonia water was added thereto with stirring under cooling on ice, the resultant mixture was dried over anhydrous sodium sulfate and the solvent was distilled off under reduced pressure. To the resultant residue, acetone (5 ml) was added, and further, ¹⁴C-methyl iodide (52 mCi/mmol) was added in an amount of 3 mCi, followed by stirring for 2 hours at room temperature. The solvent was distilled off under reduced pressure, and methylene chloride (2 ml) and trifluoroacetic acid (1 ml) were added to the resultant residue, and the resultant mixture was allowed to stand for 16 hours at room temperature. The solvent was distilled off, and methylene chloride (10 ml) and water (5 ml) were added to the resultant residue. After concentrated ammonia water was added dropwise thereto with stirring under cooling on ice to thereby make the mixture alkaline, an organic phase was separated. The organic phase was washed with water, dried over anhydrous sodium sulfate, and purified by silica gel chromatography (chloroform:methanol=15:1) to thereby obtain N-¹⁴C-methyl-3-hydroxy-4-(1-acetoxy-3-iodo-2-propenyl)piperidine (45) (12 mg, 1.8 mCi) in the form of a colorless oil.

FAB-MS(3-nitrobenzyl alcohol) [M+H]⁺ 340(¹²C), 342 (¹⁴C)

¹H-NMR(CDCl₃) δ: 1.44–1.51(1H, m), 1.60–1.75(2H, m), 2.01–2.14(2H, m), 2.11(3H, s), 2.41(3H, s), 2.98(1H, d), 3.13–3.16(1H, m), 3.53–3.58(1H, bs), 5.67(1H, d), 6.40(1H, d), 6.51(1H, dd)

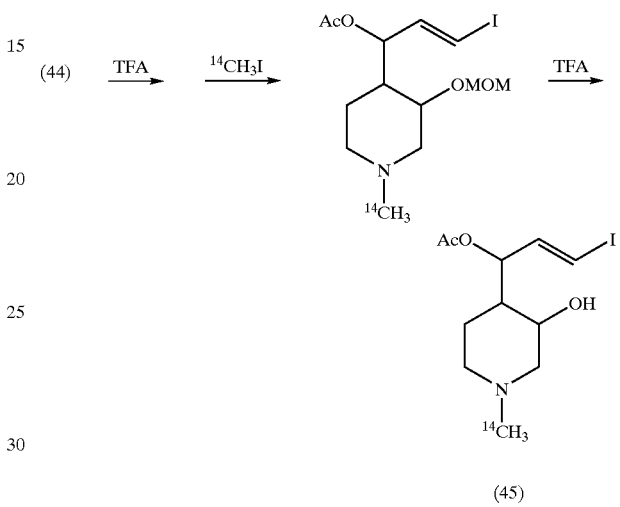

(7) To compound No.45 (1.8 mCi, 12 mg) obtained in (6), methanol (5 ml) and 10% aqueous potassium hydroxide solution (0.125 ml) were added, followed by stirring for 2 hours at room temperature. The solvent was distilled off and water was added to the resultant residue, and with salting out by an addition of sodium chloride, the resultant mixture was extracted with methylene chloride. The extract was dried over anhydrous sodium sulfate and concentrated to thereby obtain crude N-¹⁴C-methyl-3-hydroxy-4-(l-hydroxy-3-iodo-2-propenyl)piperidine (46) (1.37 mCi).

FAB-MS(3-nitrobenzyl alcohol) [M+H]⁺ 298(¹²C), 300 (¹⁴C)

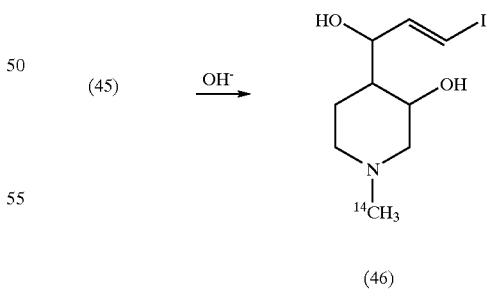

(8) To compound No. 46 (1.37 mCi) obtained in (7), pyridine (0.4 ml) and acetic anhydride (0.2 ml) were added, followed by stirring for 3 hours at room temperature. The reaction mixture was purified by silica gel chromatography (chloroform:methanol=15:1) to thereby obtain N-¹⁴C-methyl-3-acetoxy-4-(1-hydroxy-3-iodo-2-propenyl)piperidine (47) (0.82 mCi, 6 mg) in the form of an oil.

FAB-MS(3-nitrobenzyl alcohol) [M+H]$^+$ 340($^{12}$C), 342 ($^{14}$C)

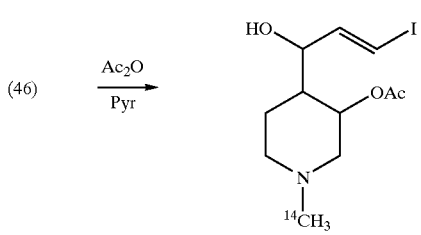

(46) →(Ac$_2$O / Pyr)

(47)

The compound No. 47 was prepared as a $^{14}$C-labeled compound. When $^{12}$C-methyl iodide was used as a raw material instead of $^{14}$C-methyl iodide, non-radioactive compound No. 47 was obtained.

Example 7

In the same manner as described in Example 6, the following compounds were obtained.

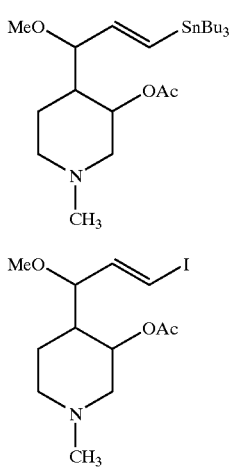

(48)

(49)

Example 8

(1) Compound No. 11 (0.1 mg) obtained in Example 1 (9) was dissolved in ethanol (50 μl), and $^{123}$I-sodium iodide (74–185 MBq), 0.1 N hydrochloride (50 μl), and 0.32% peracetic acid (50 μl) were added to the solution, after which the resultant mixture was allowed to stand for 30 minutes at room temperature with occasional stirring. To the reaction mixture, sodium metasulfite (50 μl) at a concentration of 100 mg/ml was added and further, a saturated solution of sodium carbonate (1 ml) was added. The resultant mixture was extracted with ethyl acetate. After the extract was dried over anhydrous sodium sulfate and concentrated under reduced pressure, the resultant residue was subjected to elution with an eluent (methanol:water:triethylamine=70:30:0.1) by use of HPLC (ODS C18 column) to thereby obtain two geometrical isomers (50a) and (50b) of radioactive iodide-labeled compound. Radiochemical purity of each isomer was 98% or more. The geometrical isomers (50a) and (50b) have the same retention time under HPLC and the same Rf value under TLC as do isomers (12a) and (12b) of non-radioactive compound No. 12.

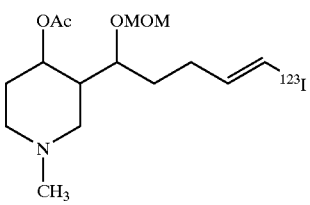

(50)

(2) To geometrical isomer No. 50b obtained in (1), trifluoroacetic acid (0.5 ml) was added, and the resultant mixture was allowed to stand for 2 hours at room temperature. The reaction mixture was evaporated to dryness under reduced pressure, and the residue was subjected to elution with an eluent (methanol:water:triethylamine=60:40:0.1) by use of HPLC (ODS C18 column) to thereby obtain radioactive iodide-labeled compound (51). The compound (51) has the same retention time under HPLC and the same Rf value under TLC as does a geometrical isomer (13b) of non-radioactive compound No. 13.

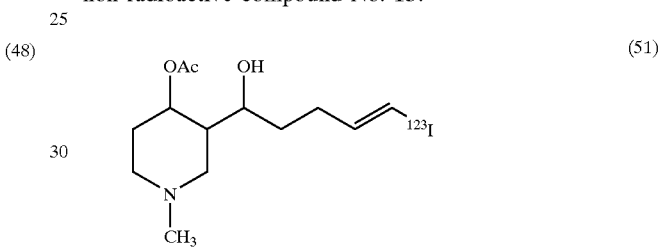

(51)

(3) In the same manner as described in (1) and (2), the following radioactive iodide-labeled compounds were obtained.

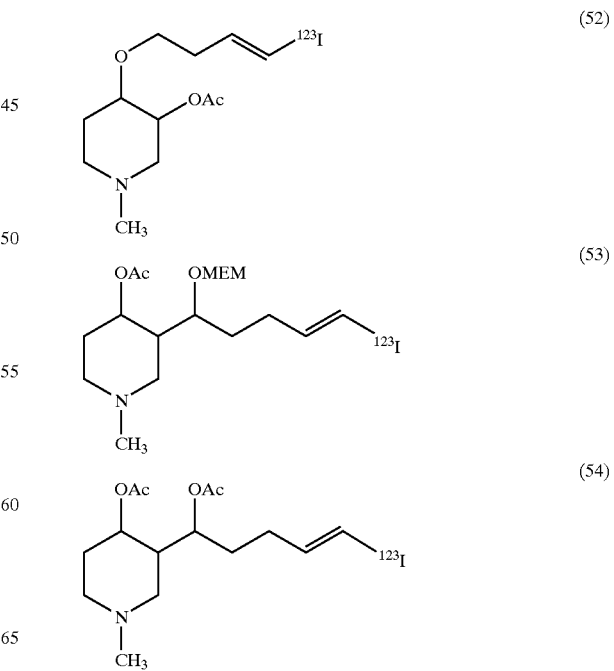

(52)

(53)

(54)

-continued

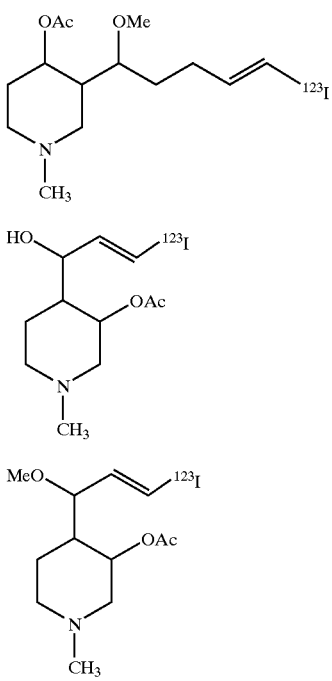

(55)
(56)
(57)

Test Example 1

(1) With respect to a geometrical isomer (50b) of compound No. 50 obtained in Example 8 (1), reactivity and specificity for AchE were examined in accordance with the following method.

Cerebral cortical tissues were obtained from rats, weighed and homogenized (90 mg tissue/ml) in 0.1 M phosphate buffer, pH7.4. To the homogenate (200 μl), a solution (20 μl) of $^{123}$I-labeled compound (50b) was added, and under incubation at 37° C. with time, hydrolysis rate was measured by use of radio TLC. Meanwhile, when BW284c51, which is a specific inhibitor for AchE, was added to the same reaction system, hydrolysis was considerably inhibited and specificity for AchE was 88.6%.

(2) With respect to compound No. 13 led from an optical isomer (7b) of compound No. 7 obtained in Example 1 (5), reactivity and specificity for AchE were examined in accordance with the following method.

Rat brain cortex was processed into a 20% (w/v) homogenate by use of 0.9% NaCl-10 mM phosphate buffer (pH 7.4). To the homogenate, there was added a $^{14}$C-labeled compound which had been prepared by substituting a carbon atom of N-methyl group in compound No. 13 with $^{14}$C, and after the incubation at 37° C., hydrolysis rate was assayed by use of radio TLC. Two different components, one having a half-life of about 5 minutes and the other having a half-life of about 10 minutes, were identified. Through individual examination of two different geometrical isomers of compound No. 13, it was confirmed that the component having the shorter half-life corresponds to an isomer (13b) and the component having the longer half-life corresponds to an isomer (13a). In contrast, when BW284c51, which is a specific inhibitor for AchE, was added to the same reaction system, hydrolysis was considerably inhibited. From the results of the inhibition test, specificity for AchE in hydrolysis reaction of isomers (13a) and (13b) were found to be 80.4% and 91.8%, respectively. Isomer (13b) exhibited excellent reactivity and specificity for AchE and it was confirmed that isomer (13b) has suitable characteristics for assaying the central AchE activity.

Test Example 2

After a geometrical isomer (50b) of compound No. 50 obtained in Example 8 (1) had been intravenously administered to groups of male wistar rats, radioactivity distribution in the rat brain was assayed by dissection method.

The results are shown in FIG. 1. Immediately after administration, radioactivity distribution in the rat brain depends on blood flow rate, which was found to be high in the brain cortex and low in the striatum. Fifteen minutes or more after administration, high accumulation of radioactivity was found in the striatum, which had remarkably high AchE activity, but accumulation of radioactivity was low in the cerebellum, which had low AchE activity. Therefore, radioactivity distribution was found to vary in accordance with AchE activity.

Test Example 3

With respect to compound No. 13 induced from an chemical isomer (7b) of compound No. 7 obtained in Example 1 (5), a $^{14}$C-labeled compound which had been prepared by substituting a carbon atom of the N-methyl group in isomer (13b) with $^{14}$C was intravenously administered to a male white rat, and radioactivity distribution in the rat brain was assayed by use of quantitative autoradiography.

Figure 2:
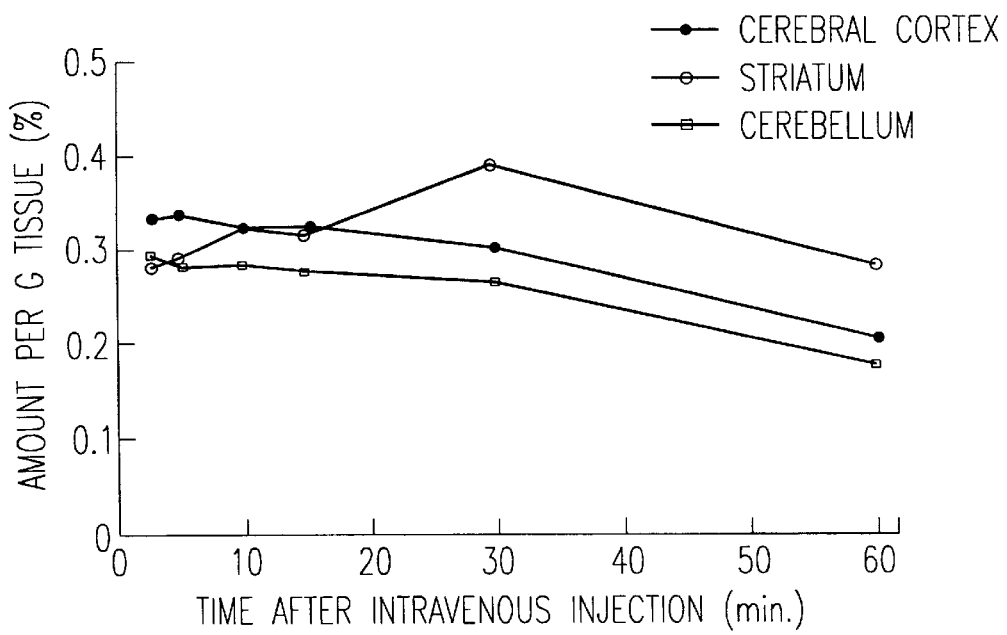
FIG. 2 shows cerebral distribution of radioactivity in rats determined by quantitative autoradiography after the administration of one of the compounds produced by the present invention.

The results are shown in FIG. 2. Immediately after administration, radioactivity distribution in the rat brain depends on quantity of blood flow, which was found to be high in the brain cortex and low in the corpus striatum. Thirty minutes or more after administration, high accumulation of radioactivity was found in the striatum, which had remarkably high AchE activity, but low accumulation of radioactivity was found in the cerebellum, which had low AchE activity. Therefore, radioactivity distribution was found to vary in accordance with AchE activity.

Tacrine (10 mg/kg), which is an inhibitor for central AchE, was orally administered to a male white rat, and 30 minutes later, a $^{14}$C-labeled compound which had been prepared by substituting a carbon atom of the N-methyl group in compound (13b) with $^{14}$C was intravenously administered to the rat, and radioactivity distribution in the rat brain was assayed by use of quantitative autoradiography. The distribution ratio of radioactivity in each part of the brain was lowered by about 30% as compared with the group to which Tacrine had not been administered.

The results show that central AchE activity relates closely to distribution of the present compound in the brain and suggest that the present compound is useful as a tracer for SPECT in assaying the central AchE activity.

Test Example 4

Compound No. 47 obtained in Example 6 (8) and compound No. 46 obtained in Example 6 (7), which is an acetylcholinesterase metabolite of compound No. 47, were intravenously administered to a male white rat, and radioactivity distribution in the rat brain was assayed by use of autoradiography.

Figure 3A:
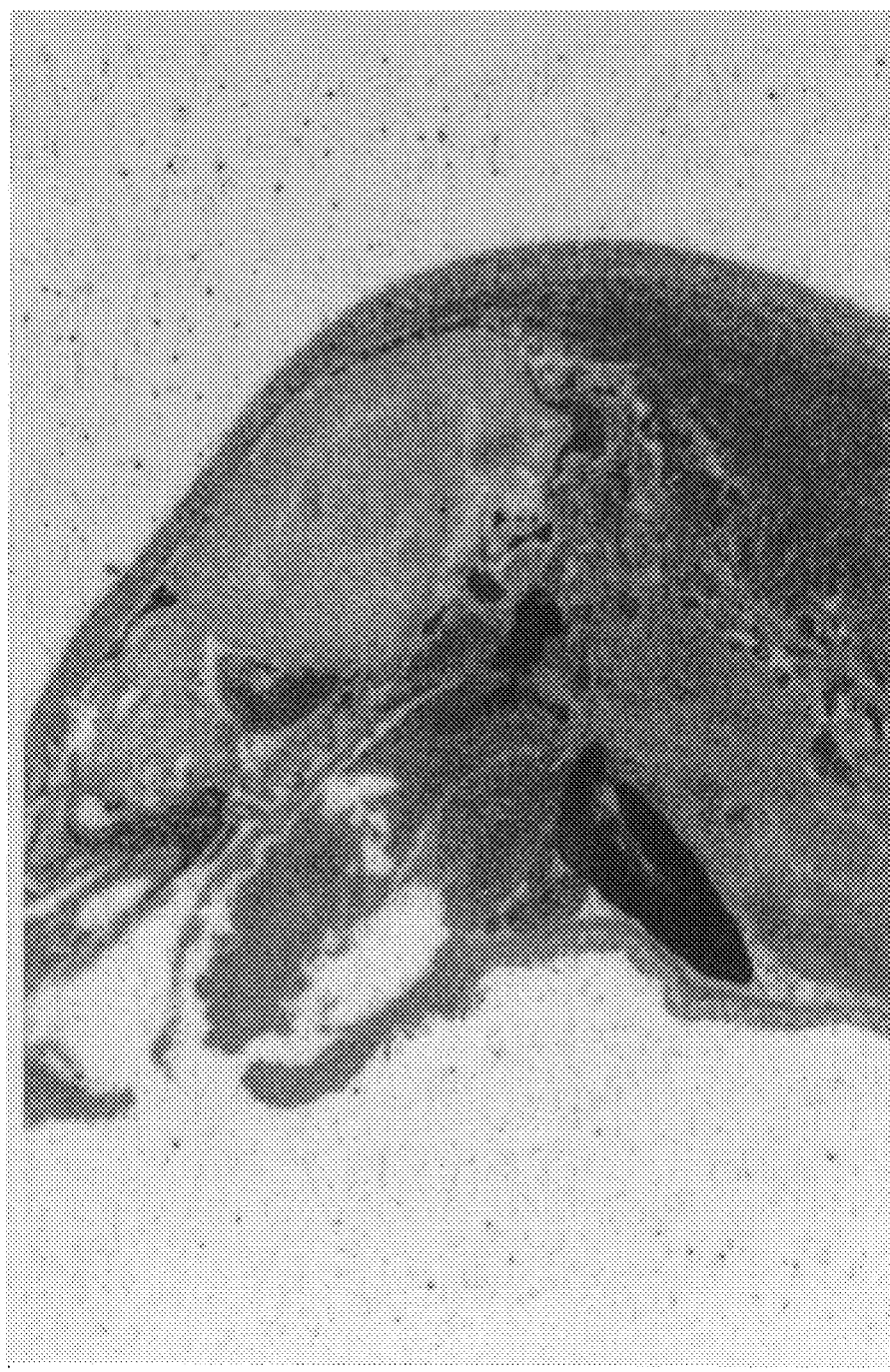
FIG. 3 shows autoradiographic images of cerebral distribution of radioactivity in rats after the administration of one of the compounds produced by the present invention.
Figure 3B:
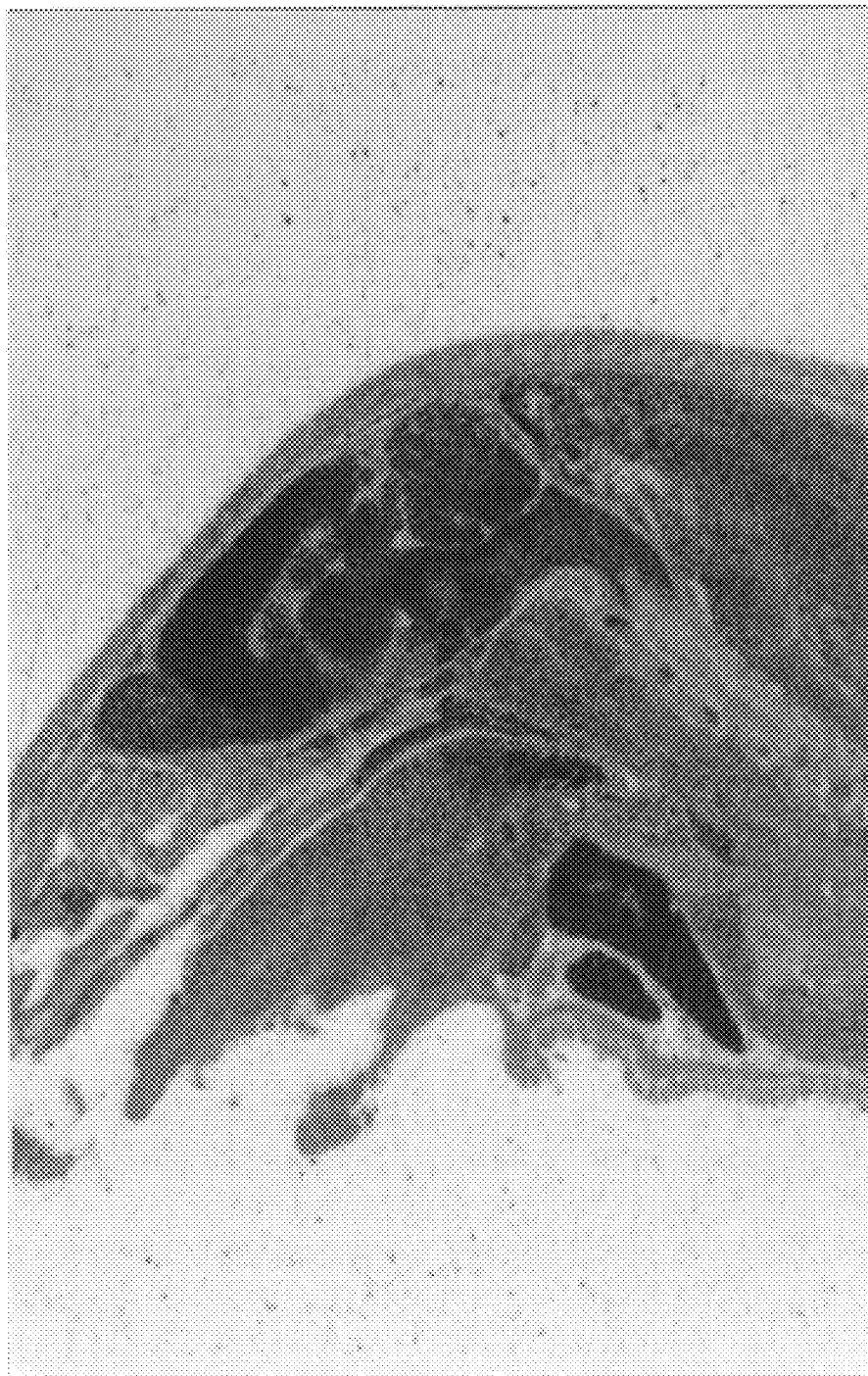
Figure 3C:
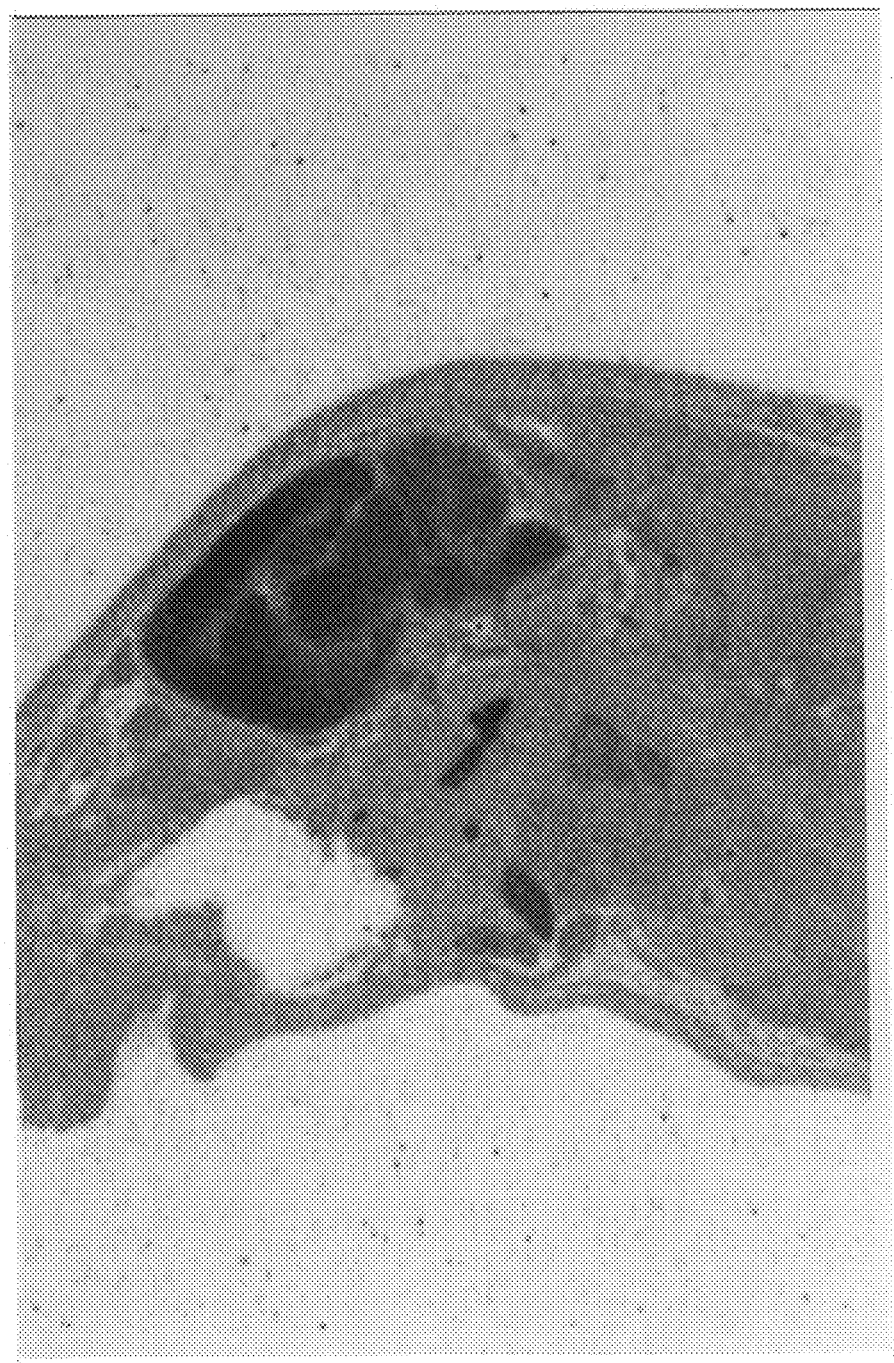

The results are shown in FIG. 3. Compound No. 46, a metabolite, hardly migrated to the brain, but compound No. 47 commonly migrated to the brain. Immediately (5 minutes later) after administration, radioactivity distribution in the rat brain depends on blood flow rate, and was found to be high in the brain cortex, somewhat high in the corpus striatum, and low in the cerebellum. Thirty minutes after administration, high accumulation of radioactivity was found in the corpus striatum, which had remarkably high AchE activity, but low accumulation of radioactivity was found in the cerebellum, which had low AchE activity. Therefore, radioactivity distribution was found to depend on AchE activity.

The results show that central AchE activity relates closely to distribution of the present compound in the brain and that the present compound is useful as a tracer for SPECT in assaying the central AchE activity.

Industrial Applicability

The compounds of the present invention have high lipophilicity, easily pass through the blood-brain barrier, are hydrolyzed specifically by AchE within the central tissue into alcohols which have low lipophilicity, which are then captured by the brain. In contrast, alcohols formed outside the brain do not migrate into the brain. The compounds of the present invention emit γ-rays at an appropriate energy level. These characteristics make the compounds highly useful as tracers for SPECT in assaying the central AchE activity.

What is claimed is:

1. A reagent for assaying AchE activity, which comprises a N-alkylpiperidine compound represented by the following formula (1) or (2) or a salt thereof:

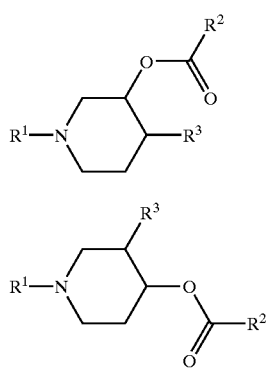

wherein $R^1$ represents an lower alkyl group which may be substituted by a fluorine atom; $R^2$ represents a lower alkyl group; and $R^3$ represents an alkenyl group which is substituted at the 1-position by a hydroxy group, a lower alkoxy group, a lower alkoxyalkyloxy group, a lower alkyoxyalkyloxyalkyloxy group, or a lower alkanoyloxy group and is substituted at an end by radioactive iodine, or an alkenyloxymethyl group which is substituted at an end by radioactive iodine or a salt thereof.

2. A reagent for assaying central local AchE activity according to claim 1, which is a reagent for use in single photon emission computed tomography (SPECT).

3. An assay method for the central local AchE activity in a subject, which comprises administering to the subject an assaying effective amount of the reagent of claim 1, measuring the radioactivity concentration in a central local site, measuring the blood flow in the cnetral local site, and computing local AchE activity on the basis of a relation between the resultant measurements and AchE activity.

4. The reagent of claim 1, wherein $R^3$ is a $C_1$–$C_5$ alkoxyl group.

5. The reagent of claim 4, wherein $R^3$ is a methoxy.

6. The reagent of claim 5, wherein $R^{3P}$ is a methoxy.

7. The reagent of claim 1, wherien $R^3$ is an alkenyl group substituted at the 1-position by a $C_1$–$C_4$alkoxy-$C_1$–$C_5$ alkoxy group.

8. The reagent of claim 7, wherein $R^3$ is an alkenyl group substituted at the 1-position by a group selected from the group consisting of methoxymethyloxy, ethoxymethloxy, and ethoxyethyloxy.

9. The reagent of claim 1, wherein $R^3$ is an alkenyl group substituted at the 1-position by a $C_1$–$C_5$ alkoxy-$C_1$–$C_5$ alkyloxy-$C_1$–$C_5$ alkyloxy group.

10. The reagent of claim 1, wherein $R^3$ is an alkenyl group substituted at the 1-position by methyoxyethyloxymethyloxy or ethoxyethyloxymethyloxy.

11. The reagent of claim 1, wherein $R^3$ is an alkenyl group substituted at the 1-position by $C_2$–$C_6$ alkanoyloxy group.

12. The reagent of claim 11, wherein $R^3$ is an alkenyl group substituted at the 1-position by acetoxy or propionyloxy.

13. The reagent of claim 1, wherein said radioactive iodine is $^{123}I$ or $^{131}I$.

14. The reagent of claim 1, wherein $R^3$ is a $C_2$–$C_8$ alkenyl group.

15. The reagent of claim 1, wherein $R^3$ is selected from the group consisting of propenyl, butenyl, and pentenyl.

16. The reagent of claim 1, wherein $R^3$ is $C_3$–$C^9$ alkenyloxymethyl group.

17. The reagent of claim 16, wherein $R^3$ wherein $R^3$ propenyloxymethyl or butenyloxymethyl.

18. The reagent of claim 1, wherein $R^3$ is a $C_2$–$C_8$ alkenyl group substituted at the 1-position by a group selected from the group consisting of hydroxy, lower alkoxyalkyloxy, lower alkoxyalkyloxyalkyloxy and a lower alkanoyloxy; and said $C_2$–$C_8$ alkenyl group substituted by at the end with radioactive iodine.

19. The reagent of claim 1, wherein the compound, wherein the compound is selected from the group consisting of:

N-Methyl-3-acetoxy-4-(hydroxy-3-$^{123}$I-2-propenyl)piperidine;

N-Methyl-3-acetoxy-4-(hydroxy-3-$^{123}$I-3-butenyl)piperidine;

N-Methyl-3-acetoxy-4-(hydroxy-3-$^{123}$I-4-pentenyl)piperidine;

N-Methyl-3-priopionoxy-4-(hydroxy-3-$^{123}$I-2-propenyl)piperidine;

N-Methyl-3-priopionoxy-4-(hydroxy-3-$^{123}$I-3-butenyl)piperidine;

N-Methyl-3-priopionoxy-4-(hydroxy-3-$^{123}$I-4-pentenyl)piperidine;

N-Methyl-3-(hydroxy-3-$^{123}$I-2-propenyl)-4acetoxypiperidine;

N-Methyl-3-(hydroxy-4-$^{123}$I-3-butenyl)-4-acetoxypiperidine;

N-Methyl-3-(hydroxy-5-$^{123}$I-4-pentenyl)-4-acetoxypiperidine;

N-Methyl-3-(hydroxy-3-$^{123}$I-2-propenyl)-4-acetoxypiperidine;

N-Methyl-3-(hydroxy-4-$^{123}$I-3-butenyl)-4-acetoxypiperidine;

N-Methyl-3-(hydroxy-5-$^{123}$I-4-pentenyl)-4-acetoxypiperidine;

N-Methyl-3-(hydroxy-3-$^{123}$I-2-propenyl)-4-propionoxypiperidine;

N-Methyl-3-(hydroxy-4-$^{123}$I-3-butenyl)-4-propionoxypiperidine;

N-Methyl-3-(hydroxy-5-$^{123}$I-4-pentenyl)-4-propionoxypiperidine;

N-Methyl-3-acetoxy-4-(1-hydroxy-3-tributylstannyl-2-propenyl)piperidine;

N-Methyl-3-acetoxy-4-(1-hydroxy-4-tributylstannyl-3-butenyl)piperidine;

N-Methyl-3-acetoxy-4-(1-hydroxy-5-tributylstannyl-4-pentenyl)piperidine;

N-Methyl-3-propionoxy-4-(1-hydroxy-3-tributylstannyl-2-propenyl)piperidine;

N-Methyl-3-propionoxy-4-(1-hydroxy-4-tributylstannyl-3-butenyl)piperidine;

N-Methyl-3-propionoxy-4-(1-hydroxy-5-tributylstannyl-4-pentenyl)piperidine;

N-Methyl-3-(1-hydroxy-3-tributylstannyl-2-propenyl)-4-acetoxypiperidine;

N-Methyl-3-(1-hydroxy-4-tributylstannyl-3-butenyl)-4-acetoxypiperidine;

N-Methyl-3-(1-hydroxy-5-tributylstannyl-4-pentenyl)-4-acetoxypiperidine;

N-Methyl-3-(1-hydroxy-3-tributylstannyl-2-propenyl)-4-propionoxypiperidine;

N-Methyl-3-(1-hydroxy-4-tributylstannyl-3-butenyl)-4-propionoxypiperidine; and

N-Methyl-3-(1-hydroxy-5-tributylstannyl-4-pentenyl)-4-propionoxypiperidine.

* * * * *

UNITED STATES PATENT AND TRADEMARK OFFICE
CERTIFICATE OF CORRECTION

PATENT NO.     : 6,509,003 B2
DATED          : January 21, 2003
INVENTOR(S)    : Irie et al.

It is certified that error appears in the above-identified patent and that said Letters Patent is hereby corrected as shown below:

Column 38,
Line 11, "claim 1" should read -- claim 9 --;
Lines 12-13, "methyoxyethyloxymethy-loxy" should read
-- methyloxyethyloxymethyloxy --;
Line 25, "$C_3$-$C^9$" should read -- $C_3$-$C_9$ --;
Line 27, "wherein $R^3$ wherein $R^3$"" should read -- wherein $R^3$ is --.
Lines 38-39, "N-Methyl-3-acetoxy-4-(hydroxy-3-$^{123}$I-2-propenyl) piperidine;" should read -- N-Methyl-3-acetoxy-4-(1-hydroxy-3-$^{123}$I-2-propenyl)piperidine; --
Lines 40-41, "N-Methyl-3-acetoxy-4-(hydroxy-3-$^{123}$I-3-butenyl) piperidine;" should read -- N-Methyl-3-acetoxy-4-(1-hydroxy-4-$^{123}$I-4-butenyl)piperidine; --
Lines 42-43, "N-Methyl-3-acetoxy-4-(hydroxy-3-$^{123}$I-4-pentenyl) piperidine;" should read -- N-Methyl-3-acetoxy-4-(1-hydroxy-5-$^{123}$I-4-pentenyl)piperidine; --
Lines 44-45, "N-Methyl-3-priopionoxy-4-(hydroxy-3-$^{123}$I-2-propenyl) piperidine;" should read -- N-Methyl-3-priopionoxy-4-(1-hydroxy-3-$^{123}$I-2-propenyl)piperidine; --
Lines 46-47, "N-Methyl-3-priopionoxy-4-(hydroxy-3-$^{123}$I-3-butenyl) piperidine;" should read -- N-Methyl-3-priopionoxy-4-(1-hydroxy-4-$^{123}$I-3-butenyl)piperidine; --
Lines 48-49, "N-Methyl-3-priopionoxy-4-(hydroxy-3-$^{123}$I-4-pentenyl) piperidine;" should read -- N-Methyl-3-priopionoxy-4-(1-hydroxy-5-$^{123}$I-4-pentenyl)piperidine; --
Lines 50-51, "N-Methyl-3-(hydroxy-3-$^{123}$I-2-propenyl) 4acetoxypiperidine;" should read -- N-Methyl-3-(1-hydroxy-3-$^{123}$I-2-propenyl)4-acetoxypiperidine; --
Lines 52-53, "N-Methyl-3-(hydroxy-4-$^{123}$I-3-butenyl)-4-acetoxypiperidine;" should read -- N-Methyl-3-(1-hydroxy-4-$^{123}$I-3-butenyl)-4-acetoxypiperidine; --
Lines 54-55, "N-Methyl-3-(hydroxy-5-$^{123}$I-4-pentenyl)-4-acetoxypiperidine;" should read -- N-Methyl-3-(1-hydroxy-5-$^{123}$I-4-pentenyl)-4-acetoxypiperidine; --
Lines 56-57, 58-59 and 60-61, delete lines
Lines 62-63, "N-Methyl-3-(hydroxy-3-$^{123}$I-2-propenyl)-4-propionoxypiperidine;" should read -- N-Methyl-3-(1-hydroxy-3-$^{123}$I-2-propenyl)-4-propionoxypiperidine; --
Lines 64-65, "N-Methyl-3-(hydroxy-4-$^{123}$I-3-butenyl)-4-propionoxypiperidine;" should read -- N-Methyl-3-(1-hydroxy-4-$^{123}$(I-3-butenyl)-4-propionoxypiperidine; --

UNITED STATES PATENT AND TRADEMARK OFFICE
CERTIFICATE OF CORRECTION

PATENT NO. : 6,509,003 B2
DATED : January 21, 2003
INVENTOR(S) : Irie et al.

It is certified that error appears in the above-identified patent and that said Letters Patent is hereby corrected as shown below:

<u>Column 39,</u>
Lines 1-2, "N-Methyl-3-(hydroxy-5-$^{123}$I-4-pentenyl)-4-propionoxypiiperidine;" should read -- N-Methyl-3-(1-hydroxy-5-$^{123}$I-4-pentenyl)-4-propionoxypiiperidine; --

Signed and Sealed this

Twelfth Day of August, 2003

JAMES E. ROGAN
*Director of the United States Patent and Trademark Office*